(12) United States Patent
Li et al.

(10) Patent No.: US 9,624,230 B2
(45) Date of Patent: Apr. 18, 2017

(54) ORGANIC COMPOUNDS

(71) Applicant: INTRA-CELLULAR THERAPIES, INC., New York, NY (US)

(72) Inventors: Peng Li, New Milford, NJ (US); Haiyan Wu, Charlotte, NC (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/671,531

(22) Filed: Mar. 27, 2015

(65) Prior Publication Data

US 2015/0197528 A1 Jul. 16, 2015

Related U.S. Application Data

(60) Continuation of application No. 13/552,381, filed on Jul. 18, 2012, now Pat. No. 9,000,001, which is a division of application No. 11/916,761, filed as application No. PCT/US2006/022066 on Jun. 6, 2006, now Pat. No. 8,273,750.

(60) Provisional application No. 60/687,715, filed on Jun. 6, 2005.

(51) Int. Cl.
*A61K 31/519* (2006.01)
*C07D 487/14* (2006.01)

(52) U.S. Cl.
CPC .................. *C07D 487/14* (2013.01)

(58) Field of Classification Search
CPC .......................... C07D 487/14; A61K 31/519
See application file for complete search history.

(56) References Cited

U.S. PATENT DOCUMENTS

| | | | |
|---|---|---|---|
| 5,202,328 A | 4/1993 | de Laszlo et al. |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 8,273,750 B2 | 9/2012 | Li et al. |
| 8,273,751 B2 | 9/2012 | Li et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 | 9/2014 | Li |
| 9,000,001 B2 | 4/2015 | Li et al. |
| 9,073,936 B2 | 7/2015 | Li et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |
| 2006/0252790 A1 | 11/2006 | Allen et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |

(Continued)

FOREIGN PATENT DOCUMENTS

DE 19931206 A1 1/2001
EP 0 063 381 A1 10/1982
(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).*
Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).*
U.S. Appl. No. 14/125,017, filed Mar. 17, 2014, Li et al.
U.S. Appl. No. 14/125,511, filed Apr. 14, 2014, Li et al.
Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, 1997, 40 (14), 2196-2210.
Al-Afaleq, E. et al., "Heterocyclic *o*-Aminonitriles: Preparation of Pyrazolo[3,4-*d*]-pyrimidines with Modification of the Substituents at the 1-Position," Molecules, 2001, 6, 621-638.
(Continued)

*Primary Examiner* — Erich A Leeser
(74) *Attorney, Agent, or Firm* — Hoxie & Associates LLC

(57) ABSTRACT

The invention provides novel 7,8-dihydro-imidazo[1,2-α]pyrazolo[4,3-e]pyrimidin-4-one compounds and 7,8,9-trihydro-[1H or 2/f]-pyrimido[1,2-a]pyrazolo[4,3-e]pyrimidin-4(5H)-one compounds, substituted at the 1 or 2 position with C2-g allcyl, C3-9 cycloalkyl, heteroarylalkyl, or substituted arylalkyl, in free, salt or prodrug form, processes for their production, their use as pharmaceuticals, particularly as PDE1 inhibitors, and pharmaceutical compositions comprising them.

19 Claims, No Drawings

(56) References Cited

U.S. PATENT DOCUMENTS

| | | |
|---|---|---|
| 2010/0273754 A1 | 10/2010 | Li |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li et al. |
| 2013/0018063 A1 | 1/2013 | Li et al. |
| 2013/0085123 A1 | 4/2013 | Li et al. |
| 2013/0239234 A1 | 9/2013 | Greengard et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0315868 A1 | 10/2014 | Li et al. |
| 2014/0357606 A1 | 12/2014 | Li |
| 2015/0038474 A1 | 2/2015 | Li et al. |
| 2015/0072965 A1 | 3/2015 | Li et al. |
| 2015/0080357 A1 | 3/2015 | Li et al. |
| 2015/0197528 A1 | 7/2015 | Li et al. |
| 2015/0259353 A1 | 9/2015 | Li et al. |
| 2016/0031895 A1 | 2/2016 | Li et al. |
| 2016/0039835 A1 | 2/2016 | Li et al. |
| 2016/0083390 A1 | 3/2016 | Li et al. |

FOREIGN PATENT DOCUMENTS

| | | |
|---|---|---|
| EP | 0 095 289 A2 | 11/1983 |
| EP | 0 201 188 A2 | 12/1986 |
| EP | 0 636 626 A1 | 2/1995 |
| EP | 0 911 333 A1 | 4/1999 |
| JP | 53031694 A | 3/1978 |
| KR | 10-1991-0006866 | 9/1991 |
| WO | WO 91/19717 A1 | 12/1991 |
| WO | WO 94/19351 A1 | 9/1994 |
| WO | WO 98/46606 A1 | 10/1998 |
| WO | WO 98/52568 A1 | 11/1998 |
| WO | WO 01/27113 A2 | 4/2001 |
| WO | WO 02/074312 A1 | 9/2002 |
| WO | WO 03/002567 A1 | 1/2003 |
| WO | WO 03/020702 A2 | 3/2003 |
| WO | WO 03/020724 A1 | 3/2003 |
| WO | WO 03/042216 A1 | 5/2003 |
| WO | WO 2006/133261 A2 | 12/2006 |
| WO | WO 2007/143568 A1 | 12/2007 |
| WO | WO 2007/143705 A2 | 12/2007 |
| WO | WO 2008/063505 A1 | 5/2008 |
| WO | WO 2008/070095 A1 | 6/2008 |
| WO | WO 2009/073210 A1 | 6/2009 |
| WO | WO 2009/075784 A1 | 6/2009 |
| WO | WO 2010/065148 A1 | 6/2010 |
| WO | WO 2010/065149 A1 | 6/2010 |
| WO | WO 2010/065151 A1 | 6/2010 |
| WO | WO 2011/043816 A1 | 4/2011 |
| WO | WO 2011/153129 A1 | 12/2011 |
| WO | WO 2011/153135 A1 | 12/2011 |
| WO | WO 2011/153136 A1 | 12/2011 |
| WO | WO 2011/153138 A1 | 12/2011 |
| WO | WO 2012/171016 A1 | 12/2012 |
| WO | WO 2013/192556 A2 | 12/2013 |
| WO | WO 2014/151409 A1 | 9/2014 |

OTHER PUBLICATIONS

"Anxiety," [retrieved on May 14, 2008]. Retrieved online via Internet, URL: http://www.nlm.nih.gov/medlineplus/anxiety.html, 5 pages.

Applicant-Initiated Interview Summary mailed Apr. 206, 2012, Notice of Allowance and Fee(s) Due mailed Apr. 26, 2012, Final Office Action mailed Mar. 27, 2012, Non-Final Office Action mailed Nov. 29, 2011, in U.S. Appl. No. 14/125,236, 27 pages.

Aswar, M. et al., "Anti-Cataleptic Activity of Various Extracts of *Ocimum sanctum*," International Journal of Pharmaceutical Research and Development, 2010, 2 (6), 7 pages.

"Autism," [retrieved on May 14, 2008]. Retrieved online via Internet, URL: http://www.nlm.nih.gov/medlineplus/autism.html, 6 pages.

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender, A. et al., "Cyclic Nucleotide Phosphodiesterases: Molecular Regulation to Clinical Use," Pharmacological Reviews, 2006, 58 (3), 488-520.

Blokland, A. et al., "PDE Inhibition and Cognition Enhancement," 2012, 22 (4), 349-354 (abstract only).

Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.

Burnouf, C. et al., "Synthesis, Structure-Activity Relationships, and Pharmacological Profile of 9-Amino-4-oxo-l-phenyl-3,4,6,7-tetrahydro[1,4]diazepino[6,7,1-*hi*]indoles: Discovery of Potent, Selective Phosphodiesterase Type 4 Inhibitors," Journal of Medicinal Chemistry, 2000, 43 (25), 4850-4867.

Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.

Chebib, M. et al., "1-Phenylpyrazolo[3,4-*d*]pyrimidines; Structure-Activity Relationships for C6 Substituents at $A_1$ and $A_{2A}$ Adenosine Receptors," Bioorganic & Medicinal Chemistry, 2000, 8, 2581-2590.

Chen, M. et al., "Effects of Bimatoprost 0.03% on Ocular Hemodynamics in Normal Tension Glaucoma," Journal of Ocular Pharmacology and Therapeutics, 2006, 22 (3), 188-193.

Chermat, R. et al., "Adaptation of the Tail Suspension Test to the Rat," Journal de Pharmacologie (Paris), 1986, 17 (3), 348-350.

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.

Dewald, H. et al., "Synthesis and Potential Antipsychotic Activity of 1*H*-Imidazo[1,2-*c*]pyrazolo[3,4-*e*]pyrimidines," Journal of Medicinal Chemistry, 1988, 31, 454-461.

Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.

Ennaceur, A. et al., "A New One-Trial Test for Neurobiological Studies of Memory in Rats. 1:Behavioral Data," Behavioural Brain Research, 1998, 31, 47-59.

Fienberg, A. et al., "DARPP-32: Regulator of the Efficacy of Dopaminergic Neurotransmission," Science, 1998, 281, 838-842.

Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.

Gelbin, M. et al., "Ketene-S,N-acetals as Synthons for Heterocycles, New Synthesis of Pyrimidinones," Journal Fiir Praktische Chemie, 1987, 329 (5), 753-766.

Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.

(56) References Cited

OTHER PUBLICATIONS

Greengard, P. et al., "Beyond the Dopamine Receptor: The DARPP-32/Protein Phosphatase-1 Cascade," Neuron, 1999, 23, 435-447.
Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.
Hulley, P. et al., "Cyclic AMP Promotes the Survival of Dopaminergic Neurons in vitro and Protects Them from the Toxic Effects of MPP+," Journal of Neural Transmission [Supplementa], 1995, 46, 217-228.
Japanese Patent Office, Patent Abstracts of Japan, Abstract for JP 53031694 A, Date of publication of application Mar. 25, 1978, 1 page.
Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, 2005, 70, 2824-2827.
Kakkar, R. et al , "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Klaissle, P. et al., "Physical Activity and Environmental Enrichment Regulate the Generation of Neural Precursors in the Adult Mouse Substantia Nigra in a Dopamine-dependent dependent Manner," BMC Neuroscience, 2012, 13, 132, doi:10.1186/1471-2202-13-132, 15 pages.
Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Lundqvist, T. et al., "Exploitation of Structural and Regulatory Diversity in Glutamate Racemases," Nature, 2007, 447, 817-822.
Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Murray, F. et al., "Expression and Activity of cAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, 2007, 292, L294-L303.
Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Pardo, C. et al., "Synthesis of 1-(p-Nitrobenzyl)Azoles and 1-(p-Nitrobenzyl)Benzazoles," OPPI Briefs, 2000, 32 (4), 385-390.

Park, E, et al., "Traumatic Brain Injury: Can the Consequences Be Stopped?" CMAJ, 2008, 178 (9), 1163-1170.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Turko, I. et al , "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brain*," Acta Physiologica Scandinavica, Supplementum 367, 1971, 1-48.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.
Wolff, M. Ed., Burger's Medicinal Chemistry and Drug Discovery, Fifth Edition, vol. I: Principles and Practice, John Wiley & Sons, New York, 1995, 975-977.
Xia, Y. et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.
Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.
Ghorab, M. et al., "Synthesis, Anticancer and Radioprotective Activities of Some New Pyrazolo[3,4-d]pyrimidines Containing Amino Acid Moieties," Arzneimittelforschung, 2009, 59 (2), 96-103.
International Search Report for International Application No. PCT/US2014/025666 mailed Jul. 7, 2014, 3 pages.
Patani, G. et al., "Bioisosterism: A Rational Approach in Drug Design," Chemical Reviews, 1996, 96 (8), 3147-3716.
Takimoto, E., "Controlling Myocyte cGMP, Phosphodiesterase 1 Joins the Fray," Circulation Research, 2009, 105, 931-933.
Written Opinion of the International Searching Authority for International Application No. PCT/US2014/025666 mailed Jul. 7, 2014, 4 pages.

* cited by examiner

ORGANIC COMPOUNDS

This application claims priority from U.S. Provisional Application No. 60/687,715, filed Jun. 6, 2005, the contents of which are hereby incorporated by reference.

TECHNICAL FIELD

The present invention relates to novel 7,8-dihydro-imidazo[1,2-a]pyrazolo[4,3-e]pyrimidin-4-one compounds and 7,8,9-trihydro-[1H or 2H]-pyrimido [1,2-a]pyrazolo[4,3-e] pyrimidin-4(5H)-one compounds, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression and damage to cognitive function, e.g., in schizophrenia.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB).

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium is linked to cell death in numerous disorders, particularly in neurodegenerative diseases such as Alzhemer's Parkinson's and Huntington's Diseases, and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, and cognitive impairment.

There is thus a need for compounds that selectively inhibit PDE1 activity, especially PDE1B activity.

SUMMARY OF THE INVENTION

The invention provides novel, optionally substituted 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form (hereinafter "Compounds of the Invention"). The 1- or 2-position substituent is preferably substituted benzyl or pyridylmethyl, e.g. para-substituted relative to the point of attachment, e.g., with aryl, e.g., phenyl, or heteroaryl, e.g., pyridyl or thiadiazolyl. These compounds are surprisingly found to selectively inhibit phosphodiesterase 1 (PDE1) activity, especially PDE1B activity.

Preferably, the Compounds of the Invention are the 7,8-dihydro-[1H or 2H]-imidazo[1,2-a]pyrazolo[4,3-e]pyrimidin-4(5H)-ones and 7,8,9-trihydro-[1H or 2H]-pyrimido[1,2-a]pyrazolo[4,3-e]pyrimidin-4(5H)-ones, of formula I

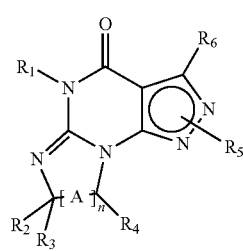

Formula 1 wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and R₃ is isopropyl), aryl, heteroaryl, (optionally hetero)arylalkoxy, or (optionally hetero)arylalkyl;
or
R₂ is H and R₃ and R₄ together form a di-, tri- or tetramethylene bridge (pref. wherein the R₃ and R₄ together have the cis configuration, e.g., where the carbons carrying R₃ and R₄ have the R and S configurations, respectively);
(iii) R₅ is a substituted heteroarylalkyl, e.g., substituted with haloalkyl or
R₅ is attached to one of the nitrogens on the pyrazolo portion of Formula 1 and is a moiety of Formula A

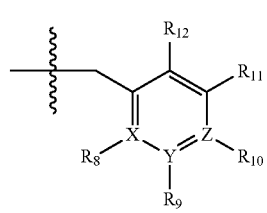

Formula A wherein X, Y and Z are, independently, N or C, and R₈, R₉, R₁₁ and R₁₂ are independently H or halogen (e.g., Cl or F), and R₁₀ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, R₈, R₉, or R₁₀, respectively, is not present; and
(iv) R₆ is H, alkyl, aryl, heteroaryl, arylalkyl (e.g., benzyl), arylamino (e.g., phenylamino), hetarylamino, N,N-dialkylamino, N,N-diarylamino, or N-aryl-N-(arylakyl)amino (e.g., N-phenyl-N-(1,1'-biphen-4-ylmethyl)amino); and
(v) n=0 or 1;
(vi) when n=1, A is —C(R₁₃R₁₄)—
wherein R₁₃ and R₁₄, are, independently, H or C₁₋₄ alkyl, aryl, heteroaryl,
(optionally hetero)arylalkoxy or (optionally hetero)arylalkyl;
in free, salt or prodrug form, including its enantiomers, diastereoisomers and racemates.

The invention further provides compounds of Formula I as follows:
1.1 Formula I wherein R₁ is methyl and n=0;
1.2 Formula I or 1.1 wherein R₄ is H or C₁₋₄ alkyl and at least one of R₂ and R₃ is lower alkyl, such that when the carbon carrying R₃ is chiral, it has the R configuration, e.g., wherein both R₂ and R₃ are methyl, or wherein one is hydrogen and the other isopropyl;
1.3 Formula I or 1.1 wherein R₄ is H and at least one of R₂ and R₃ is arylalkoxy;
1.4 Formula I wherein R₁ is methyl, R₂, R₃, and R₄ are H, n=1, and R₁₃ and R₁₄ are, independently, H or C₁₋₄ alkyl (e.g., methyl or isopropyl);
1.5 Formula I or 1.1 wherein R₂ is H and R₃ and R₄ together form a tri- or tetramethylene bridge, having the cis configuration, preferably wherein the carbons carrying R₃ and R₄ have the R and S configurations respectively;
1.6 Formula I, 1.1 or 1.5 wherein R₅ is a substituted heteroarylmethyl, e.g., para-substituted with haloalkyl;
1.7 Formula I, 1.1, 1.2, 1.3, 1.4 or 1.5 wherein R₅ is a moiety of Formula A wherein R₈, R₉, R₁₁, and R₁₂ are H and R₁₀ is phenyl;
1.8 Formula I, 1.1, 1.2, 1.3, 1.4 or 1.5 wherein R₅ is a moiety of Formula A wherein R₈, R₉, R₁₁, and R₁₂ are H and R₁₀ is pyridyl or thiadiazolyl;
1.9 Formula I, 1.1, 1.2, 1.3, 1.4 or 1.5 wherein R₅ is a moiety of Formula A wherein R₈, R₉, R₁₁, and R₁₂ are, independently, H or halogen, and R₁₀ is haloalkyl;
1.10 Formula I, 1.1, 1.2, 1.3, 1.4 or 1.5 wherein R₅ is a moiety of Formula A wherein R₈, R₉, R₁₁, and R₁₂ are, independently, H, and R₁₀ is alkyl sulfonyl;
1.11 any of the preceding formulae wherein R₅ is attached to the 2-position nitrogen on the pyrazolo ring;
1.12 any of the preceding formulae wherein R₆ is benzyl;
1.13 any of the preceding formulae wherein R₆ is phenylamino or phenylalkylamino (e.g., benzylamino);
1.14 any of the preceding formulae wherein R₆ is phenylamino;
1.15 any of the preceding formulae wherein X, Y, and Z are all C;
1.16 any of the preceding formulae wherein X, Y, and Z are all C and R₁₀ is phenyl or 2-pyridyl; and/or
1.17 any of the preceding formulae wherein the compounds inhibit phosphodiesterase-mediated (e.g., PDE1-mediated, especially PDE1B-mediated) hydrolysis of cGMP, e.g., with an IC₅₀ of less than 1 μM, preferably less than 25 nM in an immobilized-metal affinity particle reagent PDE assay, for example, as described in Example 24;
in free or salt form.

For example, the Compounds of the Invention include 7,8-dihydro-[1H or 2H]-imidazo[1,2-a]pyrazolo[4,3-e]pyrimidin-4(5H)-ones of Formula Ia

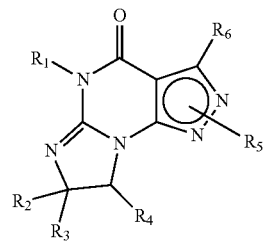

Formula Ia wherein
(i) R₁ is H or C₁₋₄ alkyl [e.g., methyl];
(ii) R₄ is H and R₂ and R₃ are, independently, H or C₁₋₄ alkyl [e.g., R₂ and R₃ are both methyl, or R₂ is H and R₃ is isopropyl], aryl, or arylalkyl;
or R₂ is H and R₃ and R₄ together form a di-, tri- or tetramethylene bridge [pref. wherein the R₃ and R₄ have the cis configuration, e.g., where the carbons carrying R₃ and R₄ have the R and S configurations respectively];
(iii) R₅ is attached to one of the nitrogens on the pyrazolo portion of formula I and is a substituted benzyl of formula B

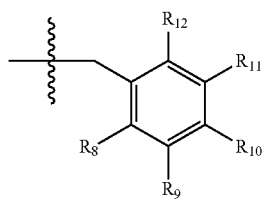

Formula B wherein $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl) aryl (e.g., phenyl), heteroaryl (e.g., pyridyl (for example pyrid-2-yl), or thiadiazolyl (e.g., 1,2,3-thiadiazol-4-yl)), arylcarbonyl (e.g., benzoyl), alkyl sulfonyl or heteroarylcarbonyl; and (iv) $R_6$ is H, alkyl, aryl, heteroaryl, arylalkyl [e.g., benzyl], arylamino [e.g., phenylamino], heteroarylamino, arylalkylamino, N,N-dialkylamino, N,N-diarylamino, or N-aryl-N-(arylalkyl)amino [e.g. N-phenyl-N-(1,1'-biphen-4-ylmethyl)amino];

in free, salt or prodrug form.

The invention further provides compounds of Formula Ia as follows:

1.1: Formula Ia wherein $R_1$ is methyl;
1.2: Formula Ia or 1.1 wherein $R_4$ is H and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
1.3: Formula Ia or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;
1.4: Formula Ia, 1.1, 1.2 or 1.3 wherein $R_5$ is a moiety of formula A wherein $R_8$, $R_9$, $R_{11}$, and $R_{12}$ are H and $R_{10}$ is phenyl;
1.5: Formula Ia, 1.1, 1.2, or 1.3 wherein $R_5$ is a moiety of formula A wherein $R_8$, $R_9$, $R_{11}$, and $R_{12}$ are H and $R_{10}$ is pyridyl or thiadiazolyl;
1.6: Formula Ia, 1.1, 1.2, 1.3, 1.4, or 1.5 wherein $R_5$ is attached to the 2-position nitrogen on the pyrazolo ring;
1.7: Formula Ia, 1.1, 1.2, 1.3, 1.4, 1.5 or 1.6 wherein $R_6$ is benzyl;
1.8: Formula Ia, 1.1, 1.2, 1.3, 1.4, 1.5 or 1.6 wherein $R_6$ is phenylamino or phenylalkylamino (e.g., benzylamino); and/or
1.9: Formula Ia, 1.1, 1.2, 1.3, 1.4, 1.5, 1.6, 1.7, or 1.8 wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 15; in free or salt form.

In an another embodiment, the Compounds of the Invention are compounds of Formula I wherein
(i) $R_1$ is methyl;
(ii) $R_2$, $R_3$ and $R_4$ are H;
(iii) n=1 and $R_a$ and $R_b$ are, independently, H or methyl;
(iv) $R_5$ is a moiety of Formula A wherein $R_8$, $R_9$, $R_{11}$ and $R_{12}$ are H and $R_{10}$ is phenyl, pyridyl (for example pyrid-2-yl), or thiadiazolyl (e.g., 1,2,3-thiadiazol-4-yl);
(v) $R_6$ is benzyl, phenylamino or benzylamino;
in free or salt form.

In another embodiment, the Compounds of the Invention are compounds of Formula I wherein
(i) $R_1$ is methyl;
(ii) n=0;
(iii) $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
(iv) $R_5$ is a substituted heteroarylmethyl, e.g., para-substituted with haloalkyl; or
$R_5$ is a moiety of Formula A wherein $R_8$, $R_9$, $R_{11}$ and $R_{12}$ are H or halogen and $R_{10}$ is haloalkyl, phenyl, pyridyl (for example pyrid-2-yl), or thiadiazolyl (e.g., 1,2,3-thiadiazol-4-yl); and
(v) $R_6$ is benzyl, phenylamino or benzylamino;
in free or salt form.

In another embodiment, the Compounds of the Invention are compounds of Formula Ia wherein
(i) $R_1$ is methyl;
(ii) $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
(iii) $R_5$ is a moiety of Formula A wherein $R_8$, $R_9$, $R_{11}$, and $R_{12}$ are H and $R_{10}$ is haloalkyl, phenyl, pyridyl (for example pyrid-2-yl), or thiadiazolyl (e.g., 1,2,3-thiadiazol-4-yl); and
(iv) $R_6$ is benzyl, phenylamino or benzylamino;
in free or salt form.

For example, Compounds of the Invention include compounds according to Formulae II, III and IV.

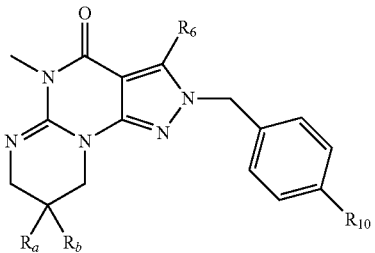

Formula II wherein
$R_a$ and $R_b$ are, independently, H or $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

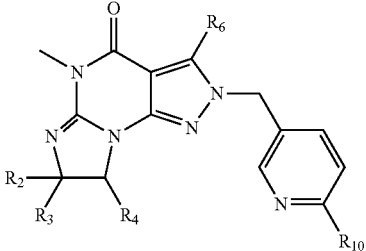

Formula III wherein
R₂ is H and R₃ and R₄ together form a tri- or tetra-methylene bridge [pref. with the carbons carrying R₃ and R₄ having the R and S configuration respectively]; or at least one of R₂ and R₃ is methyl, isopropyl or arylalkoxy and R₄ is H; or R₂ and R₃ are H and R₄ is a C₁₋₄ alkyl;
R₆ is phenylamino or benzylamino;
R₁₀ is haloalkyl, phenyl, pyridyl (for example pyrid-2-yl), or thiadiazolyl (e.g., 1,2,3-thiadiazol-4-yl);
in free or salt form.

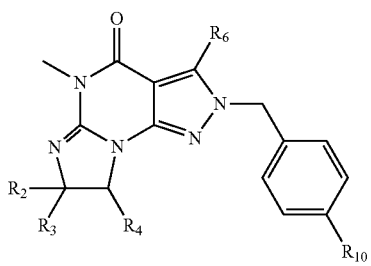

Formula IV wherein
R₂ is H and R₃ and R₄ together form a tri- or tetra-methylene bridge [pref. with the carbons carrying R₃ and R₄ having the R and S configuration respectively]; or at least one of R₂ and R₃ is methyl, isopropyl or arylalkoxy and R₄ is H; or R₂ and R₃ are H and R₄ is a C₁₋₄ alkyl;
R₆ is phenylamino or benzylamino;
R₁₀ is phenyl, pyridyl (for example pyrid-2-yl), or thiadiazolyl (e.g., 1,2,3-thiadiazol-4-yl);
in free or salt form.

Compounds of the Invention include, for example, the title compounds of Examples 1-23 below.

If not otherwise specified or clear from context, the following terms as used herein have the following meetings:
a. "Alkyl" as used herein is a saturated or unsaturated hydrocarbon moiety, preferably saturated, preferably one to four carbon atoms in length, which may be linear or branched, and may be optionally substituted, e.g., mono-, di-, or tri-substituted, e.g., with halogen (e.g., chloro or fluoro), hydroxy, or carboxy.
b. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.
c. "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).
d. "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Invention may exist in free or salt form, e.g., as acid addition salts. In this specification unless otherwise indicated language such as Compounds of the Invention is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. For example when the compounds contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. As will be appreciated the term thus embraces conventional pharmaceutical prodrug forms.

The invention also provides methods of making the Compounds of the Invention, novel intermediates useful for making Compounds of the Invention, and methods of using the Compounds of the Invention for treatment of diseases and disorders as set forth below (especially treatment of diseases characterized by reduced dopamine D1 receptor signaling activity, such as Parkinson's disease, restless leg syndrome, depression, and cognitive impairment of schizophrenia).

DETAILED DESCRIPTION OF THE INVENTION

Methods of Making Compounds of the Invention

The compounds of the formula I and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. All references cited herein are hereby incorporated in their entirety by reference.

Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

Melting points are uncorrected and (dec) indicated decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

TERMS AND ABBREVIATIONS

Bu'OH=tert-butyl alcohol,
CAN=ammonium cerium (IV) nitrate,
DIPEA=diisopropylethylamine,
DMF=N,N-dimethylforamide,
DMSO=dimethyl sulfoxide,
$Et_2O$=diethyl ether,
EtOAc=ethyl acetate,
equiv.=equivalent(s),
h=hour(s),
HPLC=high performance liquid chromatography,
$K_2CO_3$=potassium carbonate,
MeOH=methanol,
$NaHCO_3$=sodium bicarbonate,
$NH_4OH$=ammonium hydroxide,
PMB=p-methoxybenzyl,
$POCl_3$=phosphorous oxychloride,
$SOCl_2$=thionyl chloride,
TFA=trifluoroacetic acid,
THF=tetrahedrofuran.

The synthetic methods in this invention are illustrated below. The significances for the R groups are as set forth above for formula I unless otherwise indicated.

In an aspect of the invention, intermediate compounds of formula IIb can be synthesized by reacting a compound of formula IIa with a dicarboxylic acid, acetic anhydride and acetic acid mixing with heat for about 3 hours and then cooled:

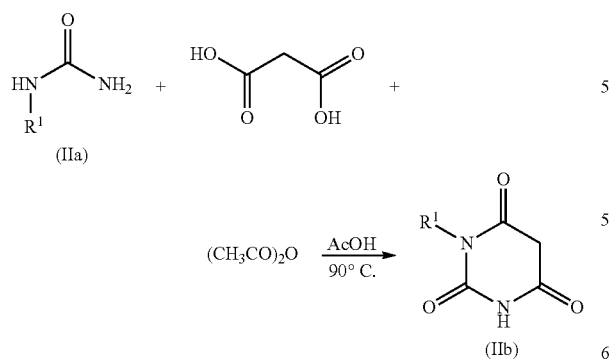

wherein $R^1$ is H or $C_{1-4}$alkyl [e.g., methyl].

Intermediate IIc can be prepared by for example reacting a compound of IIb with for example a chlorinating compound such as $POCl_3$, sometimes with small amounts of water and heated for about 4 hours and then cooled:

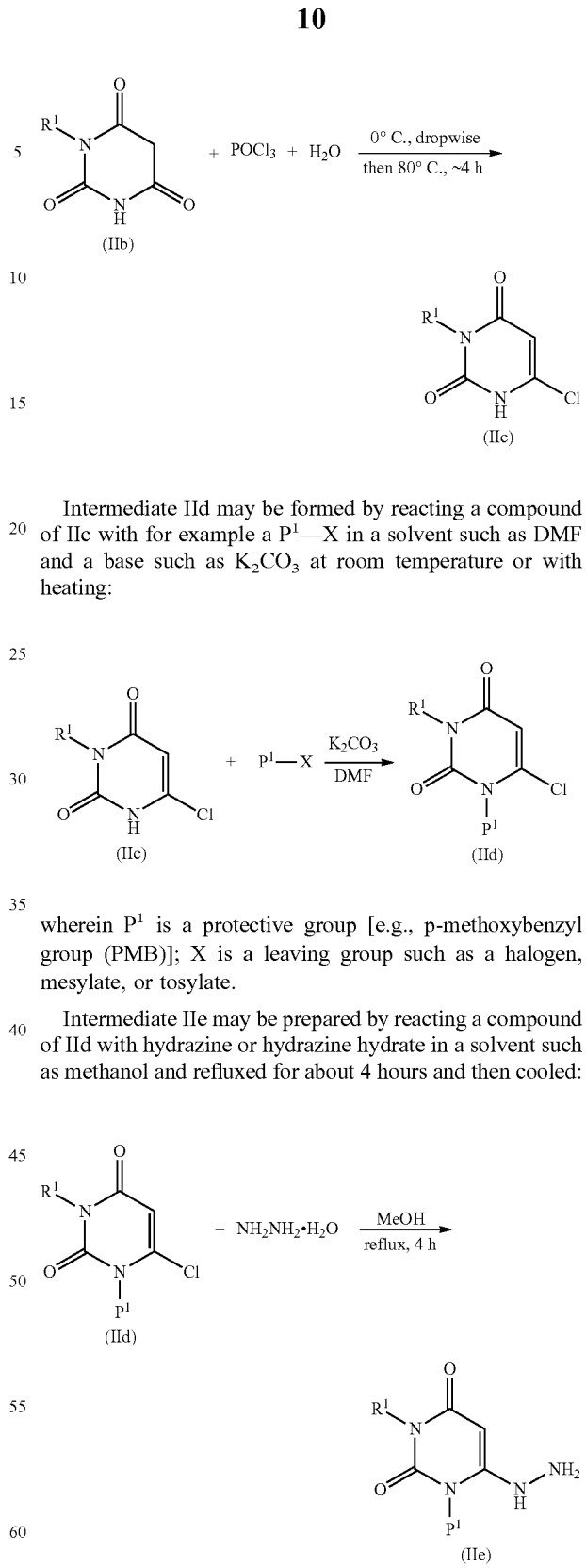

Intermediate IId may be formed by reacting a compound of IIc with for example a $P^1$—X in a solvent such as DMF and a base such as $K_2CO_3$ at room temperature or with heating:

wherein $P^1$ is a protective group [e.g., p-methoxybenzyl group (PMB)]; X is a leaving group such as a halogen, mesylate, or tosylate.

Intermediate IIe may be prepared by reacting a compound of IId with hydrazine or hydrazine hydrate in a solvent such as methanol and refluxed for about 4 hours and then cooled:

Intermediate IIf can be synthesized by reacting a compound of IIc with hydrazine or hydrazine hydrate in a solvent such as methoxymethanol and refluxed for about 30 min and then cooled:

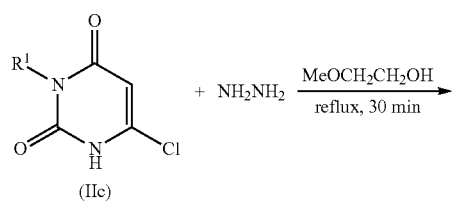

(IIc)

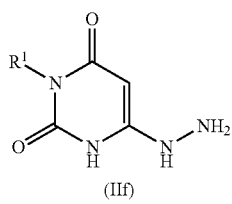

(IIf)

Intermediate IIg (wherein R¹³ is alkyl, aryl [e.g., phenyl], heteroaryl, arylalkyl, or heteroarylalkyl), can be synthesized by reacting a compound of IIe with for example an aryl isothiocyanate or isocyanate in a solvent such as DMF and heated at 110° C. for about 2 days and then cooled:

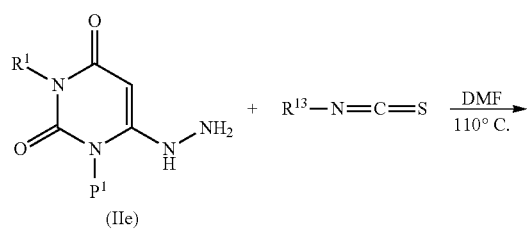

(IIe)

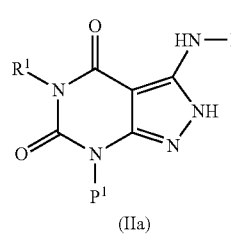

(IIa)

Intermediate IIh may be synthesized from a compound of IIg by removing the protective group P¹ with an appropriate method. For example, if P¹ is a p-methoxybenzyl group, then it can be removed with AlCl₃ at room temperature or with TFA under heated conditions. Intermediate IIh may also be prepared directly from a compound of IIf using the similar methods, but the yields are relatively low.

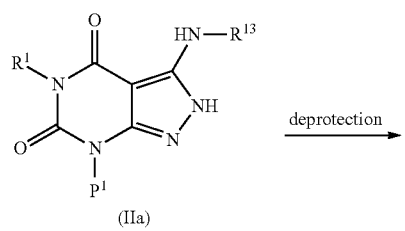 deprotection (IIa)

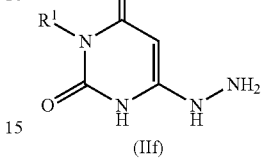

(IIf)

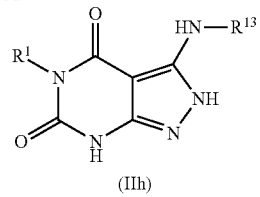

(IIh)

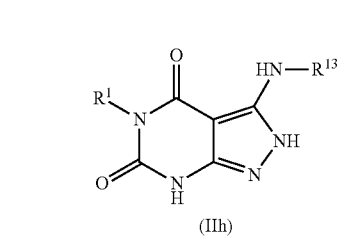

(IIh)

Intermediate II-I can be prepared by for example reacting a compound of IIh with for example a chlorinating compound such as POCl₃. The reaction may be carried out at atmospheric pressure and refluxed for about 2 days, or heated at 150–200° C. for about 10 min in a sealed vial with a microwave instrument.

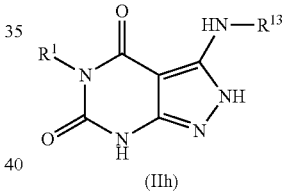

(IIh)

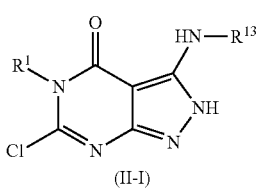

(II-I)

Intermediate IIJ can be prepared by reacting a compound of II-I with an amino alcohol under basic condition in a solvent such as DMF. The reaction may be heated overnight and then cooled:

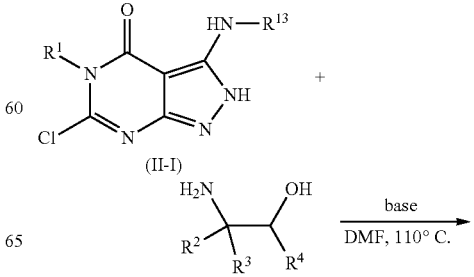

-continued

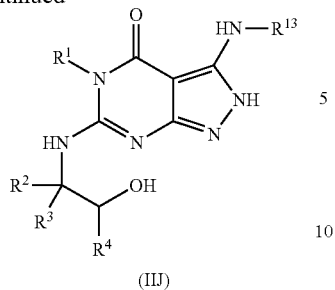

(IIJ)

Unless otherwise specified or defined, $R^2$, $R^3$ and $R^4$ are the same as those defined previously, e.g., with respect to Formula 1.

Intermediate IIK can be formed by reacting a compound of IIJ with for example a dehydrating agent such as $SOCl_2$ in a solvent such as $CH_2Cl_2$ at room temperature overnight or heated at 35° C. for about 4 hours, and then cooled:

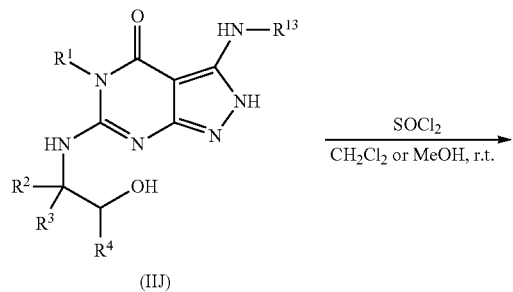

Compound Ia and Ib may be formed by reacting a compound of IIk with for example a $R^5$—X in a solvent such as DMF and a base such as $K_2CO_3$ at room temperature or with heating:

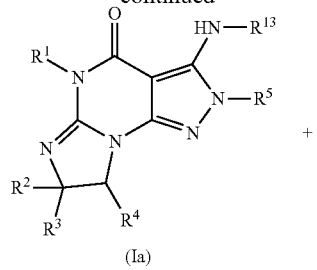

(Ia)

(Ib)

wherein $R^5$ is as defined previously [e.g. an optionally substituted benzyl group]; X is a leaving group such as a halogen, mesylate, or tosylate.

$R^5$ may also be introduced earlier by for example reacting IIg with $R^5$X and then perform similar procedure as described above to form compound Ia and Ib, as long as $R^5$ will not be cleaved off in the $P^1$ deprotection step.

The second synthetic route is designated for the preparation of compound Ia and Ib wherein $R^6$ is an alkyl, aryl or heteroaryl group.

Intermediate IIIa (wherein $R^7$ is aryl, preferably phenyl substituted with $R_{8-12}$ corresponding to the substituted benzyl of Formula A supra) may be formed by reacting a compound of IIe with an aldehyde $R^7$CHO in a solvent such as EtOAc at 0° C. or room temperature:

(IIe)

(IIIa)

Intermediate IIIb can be prepared by for example reacting a compound of IIIa with for example an aldehyde in a solvent such as DMF and heated overnight and then cooled:

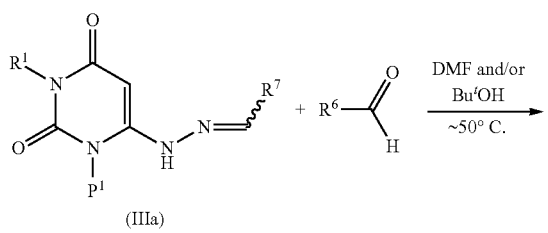

(IIIa)

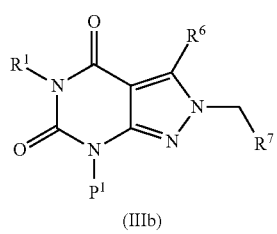

(IIIb)

Intermediate IIIc may be synthesized from a compound of IIIb by removing the protective group $P^1$ with an appropriate method. For example, if $P^1$ is a p-methoxybenzyl group, then it can be removed with CAN at room temperature. Intermediate IIIc may also be prepared directly from a compound of IIf using similar methods, but the yields are relatively low.

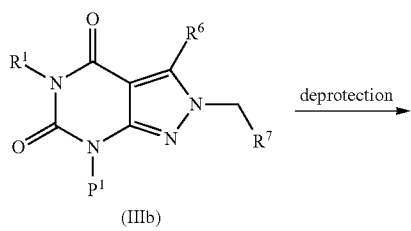

(IIIb)

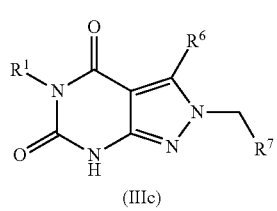

(IIIc)

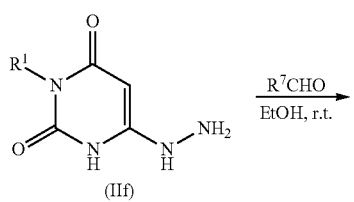

(IIf)

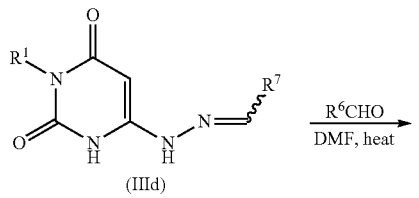

(IIId)

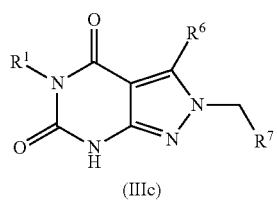

(IIIc)

Intermediate IIIe can be prepared by reacting a compound of IIIc with for example a chlorinating compound such as POCl$_3$. The reaction may be carried out at atmospheric pressure and refluxed for about 2 days, or heated at 150~200° C. for about 10 min in a sealed vial with a microwave instrument.

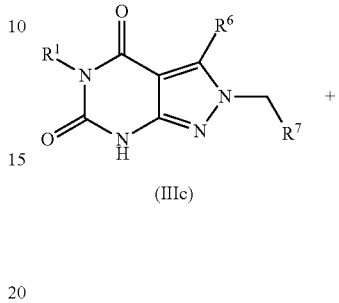

(IIIc)

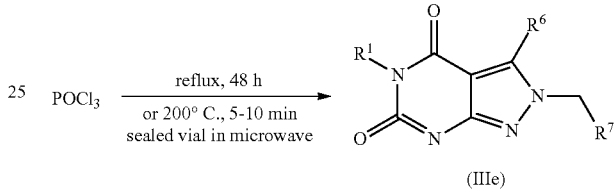

(IIIe)

Intermediate IIIf can be formed by reacting a compound of IIIe with an amino alcohol under basic condition in a solvent such as DMF and heated overnight and then cooled:

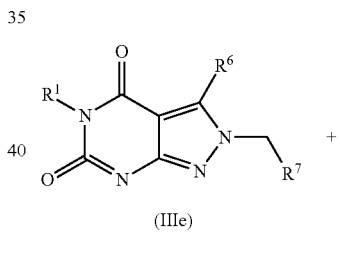

(IIIe)

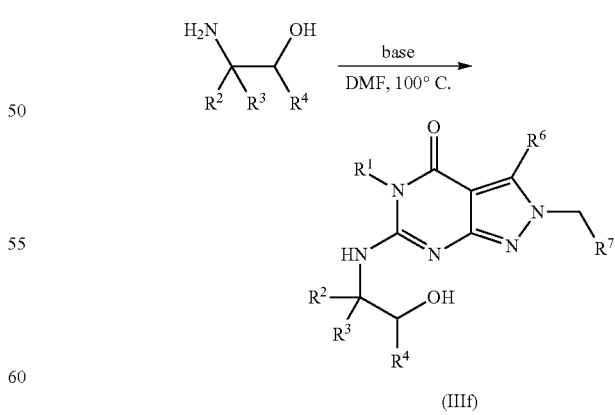

(IIIf)

Compound Ia can be formed by reacting a compound of IIIf with for example a dehydrating agent such as SOCl$_2$ in a solvent such as CH$_2$Cl$_2$ at room temperature overnight or heated at 35° C. for about 4 hours, and then cooled:

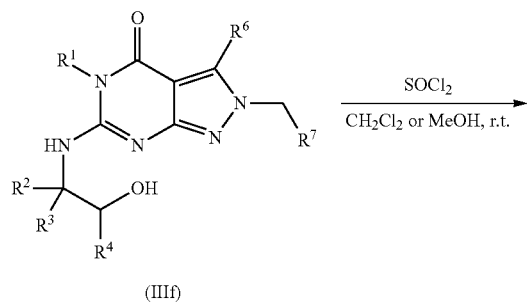

(IIIf)

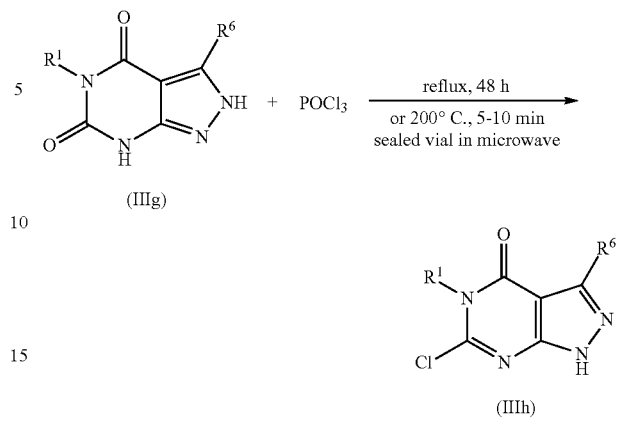

(IIIg)

(IIIh)

Intermediate III-I can be formed by reacting a compound of IIIh with an amino alcohol under basic condition in a solvent such as DMF and heated overnight and then cooled:

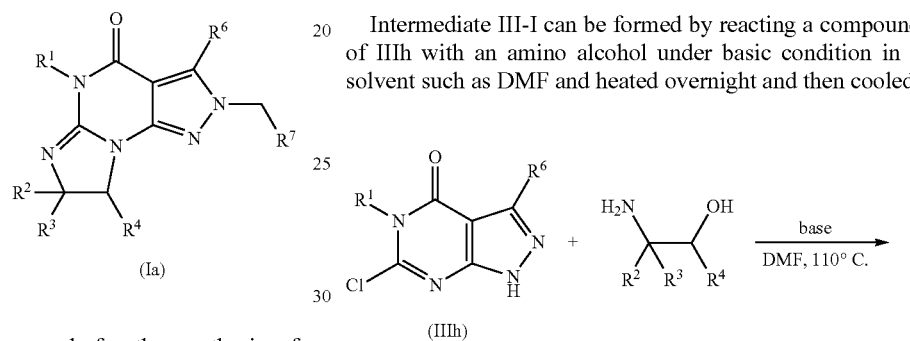

(IIIh)

(Ia)

There is an alternative approach for the synthesis of compound Ia and Ib wherein $R^6$ is an alkyl or aryl group. If a harsher condition is employed for the deprotection of IIIb, then the $R^7CH_2$ group can be cleaved off too. For instance, if $P^1$ is a p-methoxybenzyl group and $R^7$ is a substituted phenyl group, then both $P^1$ and $R^7CH_2$ can be cleaved with $AlCl_3$ at room temperature. Thus, Intermediate IIIg may be formed with this approach:

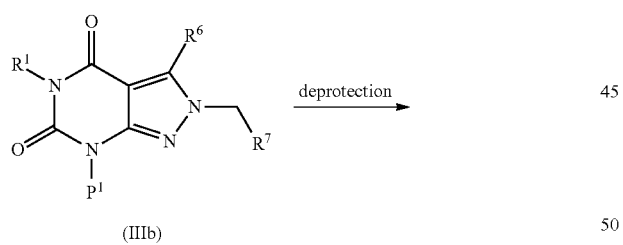

(IIIb)

(III-I)

Intermediate IIIJ may be formed by reacting a compound of III-I with for example a dehydrating agent such as $SOCl_2$ in a solvent such as $CH_2Cl_2$ or methanol at room temperature overnight or heated at 35° C. for about 4 hours, and then cooled:

(IIIg)

Intermediate IIIh can be prepared by reacting a compound of IIIg with for example a chlorinating compound such as $POCl_3$. The reaction may be carried out at atmospheric pressure and refluxed for about 2 days, or heated at 150~200° C. for about 10 min in a sealed vial with a microwave instrument.

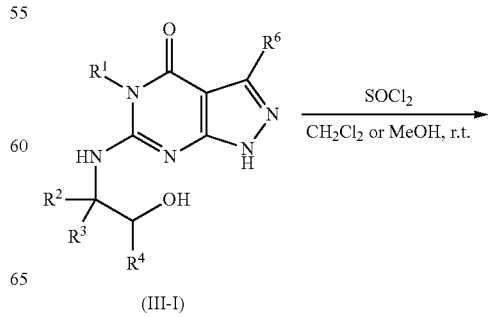

(III-I)

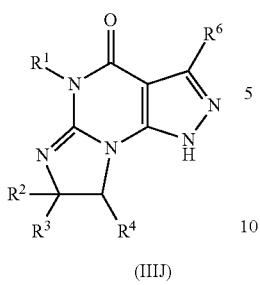

(IIIJ)

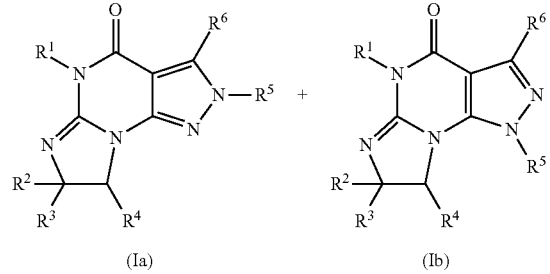

(Ia)    (Ib)

Intermediate IIIJ may also be formed by reacting a compound of Ia with for example a strong acid or Lewis acid such as AlCl₃:

The third synthetic route is designated for the preparation of compound Ia and Ib wherein $R^6$ is hydrogen.

Intermediate IVa may be formed by for example reacting a compound of IIe with POCl₃ and DMF:

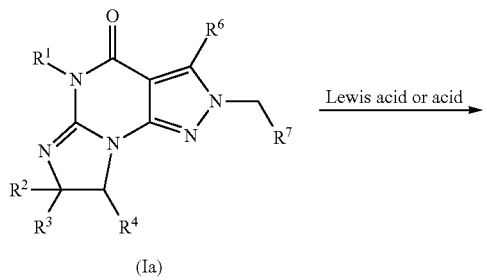

(Ia)

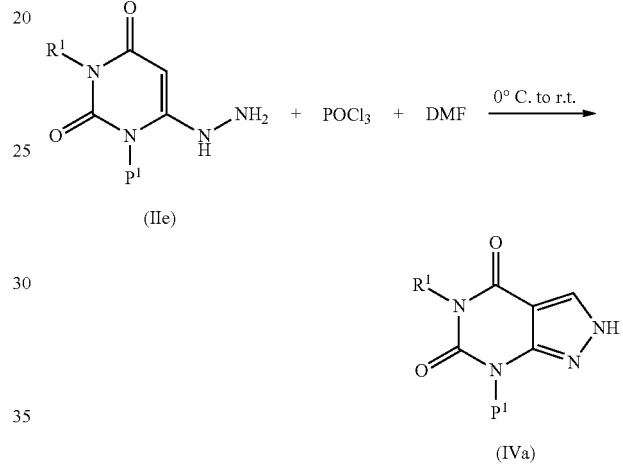

(IIe)

(IVa)

Intermediate IVb may be formed by reacting a compound of IVa with for example a $R^5$—X in a solvent such as DMF and a base such as $K_2CO_3$ at room temperature or with heating:

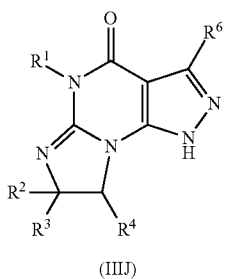

(IIIJ)

Compound Ia and Ib may be formed by reacting a compound of IIIJ with for example a $R^5$—X in a solvent such as DMF and a base such as $K_2CO_3$ at room temperature or with heating:

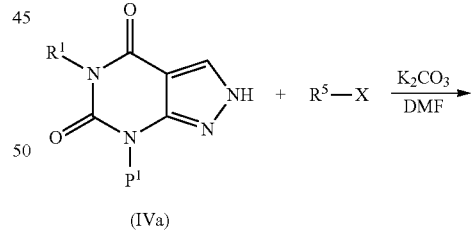

(IVa)

(IVb)

Intermediate IVc may be synthesized from a compound of IVb by removing the protective group $P^1$ with an appropriate method. For example, if $P^1$ is a PMB group, then it can be removed with CAN at room temperature:

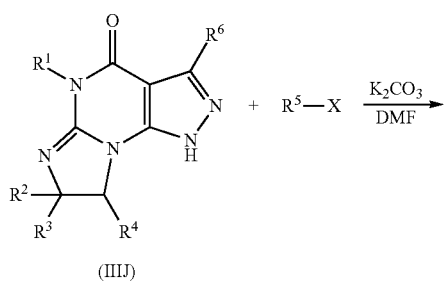

(IIIJ)

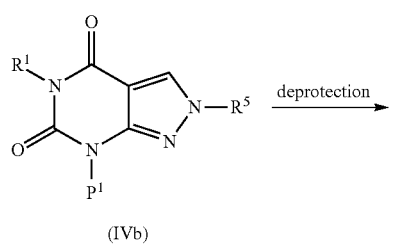

(IVb)

deprotection →

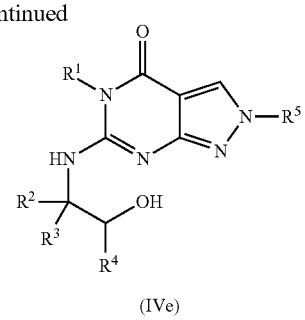

(IVe)

Compound Ia may be formed by reacting a compound of IVe with for example a dehydrating agent such as $SOCl_2$ in a solvent such as $CH_2Cl_2$ at room temperature overnight or heated at 35° C. for about 4 hours, and then cooled. Similar to the methods described above, the $R^5$ group in a compound of Ia can be cleaved off using an appropriate method, and then the obtained intermediate can react with another $R^5X$ to give compound Ia and Ib.

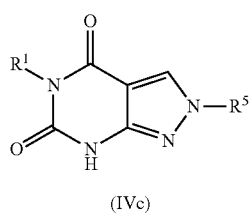

(IVc)

Intermediate IVd can be prepared by reacting a compound of IVc with for example a chlorinating compound such as $POCl_3$ and refluxed for about 2 days, or heated at 150~200° C. for about 10 min in a sealed vial with a microwave instrument and then cooled:

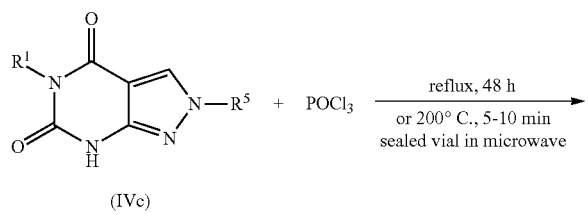

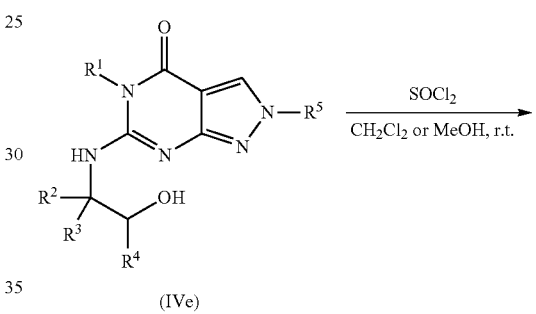

(IVe)

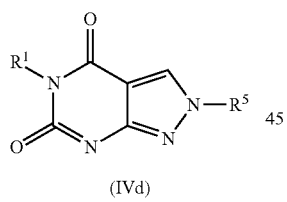

(IVd)

Intermediate IVe can be formed by reacting a compound of IVd with an amino alcohol under basic condition in a solvent such as DMF and heated overnight then cooled:

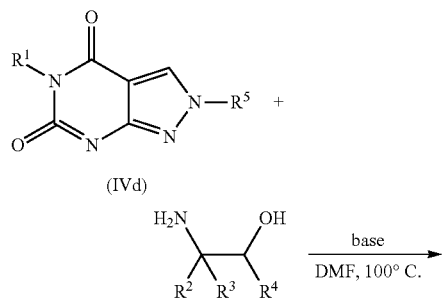

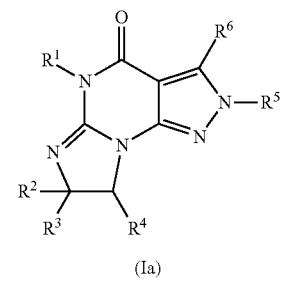

(Ia)

The invention thus provides methods of making Compounds of the Invention as described above, for example, comprising (i) reacting a 7,8-dihydro-imidazo[1,2-a]pyrazolo[4,3-e]pyrimidin-4(5H)-one or a 7,8,9-trihydro-[1H or 2H]-pyrimido[1,2-a]pyrazolo[4,3-e]pyrimidin-4(5H)-one with a compound of formula X—$R_5$ wherein X is a leaving group, e.g., halogen, mesylate, or tosylate, and $R_5$ is $C_{2-9}$ alkyl, $C_{3-9}$ cycloalkyl, heteroarylalkyl, or substituted arylalkyl, for example wherein $R_5$ is a substituted benzyl of formula A as defined above, e.g., under basic conditions, for example wherein the 7,8-dihydro-imidazo[1,2-a]pyrazolo[4,3-e]pyrimidin-4(5H)-one is a compound of Formula IIIJ:

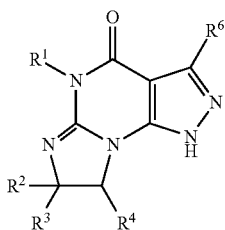

(IIIJ)

wherein $R_{1-6}$ are as defined above, e.g., with reference to Formula I; and for (ii) dehydrating a compound of Formula V

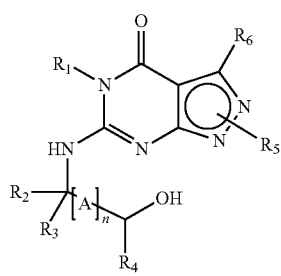

V wherein $R_{1-6}$ and $[A]_n$ are as defined above, e.g., with reference to Formula I, e.g., using a dehydrating agent, for example thionyl chloride;
and isolating the Compound of the Invention thus obtained.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:
(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, cognitive impairment, dementia, psychostimulant withdrawal, and drug addiction;
(iii) Circulatory and cardiovascular disorders, including cerebrovascular disease, stroke, congestive heart disease, hypertension, pulmonary hypertension, and sexual dysfunction;
(iv) Respiratory and inflammatory disorders, including asthma, chronic obstructive pulmonary disease, and allergic rhinitis, as well as autoimmune and inflammatory diseases; and/or
(v) Any disease or condition characterized by low levels of cAMP and/or cGMP (or inhibition of cAMP and/or cGMP signaling pathways) in cells expressing PDE1. comprising administering an effective amount of a Compound of the Invention to a human or animal patient in need thereof.

The invention also provides a method for enhancing or potentiating dopamine D1 intracellular signaling activity in a cell or tissue comprising contacting said cell or tissue with an amount of a Compound of the Invention sufficient to inhibit PDE1B activity.

The invention also provides a method for treating a PDE1-related, especially PDE1B-related disorder, or a dopamine D1 receptor intracellular signaling pathway disorder, in a patient in need thereof comprising administering to the patient an effective amount of a Compound of the Invention that inhibits PDE1B, wherein PDE1B activity modulates phosphorylation of DARPP-32 and/or the GluR1 AMPA receptor.

The present invention also provides
(i) a Compound of the Invention for use as a pharmaceutical, for example for use in any method or in the treatment of any disease or condition as hereinbefore set forth,
(ii) the use of a Compound of the Invention in the manufacture of a medicament for treating any disease or condition as hereinbefore set forth, and
(iii) a pharmaceutical composition comprising a Compound of the Invention in combination or association with a pharmaceutically acceptable diluent or carrier.

The words "treatment" and "treating" are to be understood accordingly as embracing prophylaxis and treatment or amelioration of symptoms of disease as well as treatment of the cause of the disease Compounds of the Invention are in particular useful for the treatment of Parkinson's disease.

Compounds of the Invention may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

2-(Biphenyl-4-ylmethyl)-7,8-dihydro-5,7,7-trimethyl-[2H]-imidazo-[1,2-a]pyrazolo[4,3-e]pyrimidin-4(5H)-one

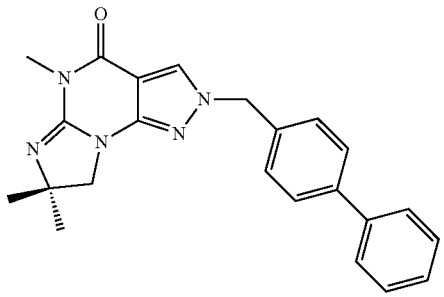

(a) 1-Methylpyrimidine-2,4,6(1H,3H,5H)-trione

To a solution of malonic acid (80 g, 0.79 mol) and methylurea (50 g, 0.68 mol) in 180 ml of acetic acid at 70° C., acetic anhydride (130 ml, 1.37 mol) is added slowly. After the completion of the addition, the reaction mixture is stirred at 90° C. for 3 hours, and then cooled to room temperature. The solvent is removed under reduced pressure, and the residue is treated with 350 mL of ethanol to precipitate out yellowish solid. The solid is recrystallized from ethanol to give 63.1 g product as crystalline solids (Yield: 65.8%). m.p.=131.2-133.1° C. [Lit.[1]: m.p.=130-131.5° C.].

(b) 6-Chloro-3-methylpyrimidine-2,4(1H,3H)-dione

Water (2.7 mL) is added dropwise to a suspension of 1-methylpyrimidine-2,4,6(1H,3H,5H)-trione (14.2 g, 100 mol) in $POCl_3$ (95 mL) at 0° C. The reaction mixture is then heated at 80° C. for 5 hours. The resulting brownish solution is cooled, and $POCl_3$ is evaporated under reduced pressure. The residue is treated with MeOH, and the obtained solid is recrystallized from ethanol to give 11.5 g product (Yield: 71.6%). m.p.=279-282° C. (dec) [Lit.[2]: 280-282° C.]. $^1$H NMR (400 MHz, DMSO-$d_6$) δ3.10 (S, 3H), 5.90 (S, 1H), 12.4 (br, 1H).

(c) 6-Chloro-1-(4-methoxybenzyl)-3-methylpyrimidine-2,4(1H,3H)-dione

A mixture of 6-chloro-3-methylpyrimidine-2,4(1H,3H)-dione (16.2 g, 101 mmol), p-methoxybenzyl chloride (16.5 mL, 122 mmol) and potassium carbonate (7.0 g, 50.7 mmol) in anhydrous DMF (200 mL) is heated at 60° C. for 3 hours. Additional potassium carbonate (3.0 g, 21.7 mmol) is added, and the reaction mixture heated at 60° C. for another 3 hours. After hot filtration, the filtrate is evaporated to dryness under reduced pressure. The obtained oil is directly used for the synthesis in the next step. A small amount of product is further purified by silica-gel flash chromatography to give pure product as crystals. $^1$H NMR (400 MHz, MeOH-$d_4$) δ3.37 (s, 3H), 3.83 (s, 3H), 5.24 (s, 2H), 5.96 (s, 1H), 6.91 and 7.32 (AB, 4H, J=6.8 Hz). MS (FAB) m/z 281.23 $[M+H]^+$.

(d) 6-Hydrazinyl-1-(4-methoxybenzyl)-3-methylpyrimidine-2,4(1H,3H)-dione

To a solution of 6-chloro-1-(4-methoxybenzyl)-3-methylpyrimidine-2,4(1H,3H)-dione (2.4 g 8.6 mmol) in EtOH (25 mL) and MeOH (50 mL), anhydrous hydrazine (1.2 mL) is added slowly. The reaction mixture is refluxed for three hours, and then cooled. A large amount of ether is added into the reaction mixture, and then filtered to give 2.0 g of product as crystalline solids (Yield: 84%). $^1$H NMR (DMSO-$d_6$) δ 3.13 (s, 3H), 3.73 (s, 3H), 4.42 (br, 1H), 5.03 (s, 2H), 5.15 (s, 1H), 6.88 and 7.15 (AB, 4H, J=6.4 Hz), 8.08 (br, 1H). MS (FAB) m/z 277.28 $[M+H]^+$.

(e) 7-(4-Methoxybenzyl)-5-methyl-1H-pyrazolo[3,4-d]pyrimidine-4,6(5H,7H)-dione

To a solution of 6-hydrazinyl-1-(4-methoxybenzyl)-3-methylpyrimidine-2,4(1H,3H)-dione (0.45 g, 1.6 mmol) in DMF (2 mL), $POCl_3$ (0.3 mL, 3.3 mmol) is added dropwise at 0° C. After the reaction mixture is stirred at 0° C. for 1 hour, the mixture is treated with methanol carefully to give white solid. The solid is further purified by chromatography to give 0.4 g product (Yield: 85%). $^1$H NMR (DMSO-$d_6$) δ 3.23 (s, 3H), 3.71 (s, 3H), 5.05 (s, 2H), 6.85 and 7.31 (AB, 4H, J=11.6 Hz), 8.47 (s, 1H), 13.5 (br, 1H). MS (FAB) m/z 287.21 $[M+H]^+$.

(f) 2-(Biphenyl-4-ylmethyl)-7-(4-methoxybenzyl)-5-methyl-2H-pyrazolo[3,4-d]pyrimidine-4,6(5H,7H)-dione A mixture of 7-(4-methoxybenzyl)-5-methyl-1H-pyrazolo[3,4-d]pyrimidine-4,6(5H,7H)-dione (0.312 g, 1.09 mmol), p-biphenylmethyl bromide (0.296 g, 1.20 mmol) and potassium carbonate (0.151 g, 1.09 mmol) in acetone (20 mL) is stirred at room temperature overnight. The solvent is evaporated under reduced pressure. The residue is directly purified by chromatography to give 0.382 g product as white solids (Yield: 77.5). $^1$H NMR (400 MHz, $CDCl_3$) δ 3.37 (s, 3H), 3.75 (s, 3H), 5.15 (s, 2H), 5.34 (s, 2H), 6.81 (m, 2H), 7.27 (m, 3H), 7.47 (m, 4H), 7.60 (m, 4H), 7.87 (s, 1H). MS (FAB) m/z 453.3 $[M+H]^+$.

(g) 2-(Biphenyl-4-ylmethyl)-5-methyl-2H-pyrazolo[3,4-d]pyrimidine-4,6(5H,7H)-dione To a solution of 2-(biphenyl-4-ylmethyl)-7-(4-methoxybenzyl)-5-methyl-2H-pyrazolo[3,4-d]pyrimidine-4,6(5H,7H)-dione (300 mg, 0.663 mmol) in THF (9 mL), a solution of ammonium cerium (IV) nitrate (1.82 g, 3.32 mmol) in water (3 mL) is added. The resulting orange solution is stirred at room temperature overnight. Another batch of CAN (1.82 g, 3.32 mmol) is added and the mixture is stirred for 6 hours, and then the third batch of CAN (1.82 g) is added, and the mixture is stirred at r.t. overnight. The reaction mixture is evaporated to dryness. The residue is treated with brine, and extracted with methylene chloride five times. The organic phase is combined and concentrated.

The residue is purified by chromatography to give product as white solids with a high yield. $^1$H NMR (400 MHz, DMDO-d$_6$) δ3.16 (s, 3H), 5.37 (s, 2H), 7.38 (m, 3H), 7.46 (m, 2H), 7.65 (m, 4H), 8.59 (s, 1H), 11.6 (s, 1H). MS (FAB) m/z 333.3 [M+H]$^+$.

(h) 2-(Biphenyl-4-ylmethyl)-6-chloro-5-methyl-2H-pyrazolo[3,4-d]pyrimidin-4(5H)-one 2-(biphenyl-4-ylmethyl)-5-methyl-2H-pyrazolo[3,4-d]pyrimidine-4,6(5H,7H)-dione (25 mg, 0.075 mmol) is refluxed in POCl$_3$ (10 mL) for 60 hours, and the mixture is evaporated to dryness. The residue is purified by silica gel flash chromatography to give 26 mg product as white solids (Yield: 98.5%). $^1$H NMR (400 MHz, CDCl$_3$) δ3.68 (s, 3H), 5.45 (s, 2H), 7.39 (m, 3H), 7.43 (m, 2H), 7.59 (m, 4H), 8.01 (s, 1H). MS (FAB) m/z 351.2 [M+H]$^+$.

(i) 2-(Biphenyl-4-ylmethyl)-6-(1-hydroxy-2-methyl-propan-2-ylamino)-5-methyl-2H-pyrazolo[3,4-d]pyrimidin-4(5H)-one A solution of 2-(biphenyl-4-ylmethyl)-6-chloro-5-methyl-2H-pyrazolo[3,4-d]pyrimidin-4(5H)-one (26 mg, 0.074 mmol) and 2-amino-2-methyl-1-propanol (71 μL, 0.74 mmol) in DMF (1 mL) is heated at 110° C. overnight. The reaction mixture is then purified by chromatography to give 21.1 mg product (Yield: 71%). MS (FAB) m/z 404.2 [M+H]$^+$.

(j) 2-(Biphenyl-4-ylmethyl)-7,8-dihydro-5,7,7-trimethyl-[2H]-imidazo-[1,2-a]pyrazolo[4,3-e]pyrimidin-4(5H)-one To a solution of 2-(biphenyl-4-ylmethyl)-6-(1-hydroxy-2-methylpropan-2-ylamino)-5-methyl-2H-pyrazolo[3,4-d]pyrimidin-4(5H)-one (17 mg, 0.042 mmol) in methylene chloride (1 mL), is added 2.0 M CH$_2$Cl$_2$ solution of thionyl chloride (63 μL, 0.126 mmol) under argon. The reaction mixture is stirred at r.t. overnight. The reaction is quenched with 5% NaHCO$_3$, and the resulting mixture is purified by chromatography to give 11 mg of the final product as white solids (Yield: 68%). $^1$H NMR (400 MHz, DMSO-d$_6$+CDCl$_3$) δ1.36 (s, 6H), 3.30 (s, 3H), 3.69 (s, 2H), 5.30 (s, 2H), 7.36 (m, 3H), 7.43 (m, 2H), 7.58 (m, 4H), 8.10 (s, 1H). MS (FAB) m/z 386.1 [M+H]$^+$.

Example 2

Cis-(6aR*,10aS*)-1-(4-Benzoylbenzyl)-5,6a,7,8,9,10,10a-heptahydro-5-methyl-3-(phenylamino)cyclohex[4,5]imidazo[1,2-a]pyrazolo[4,3-e]pyrimidin-4 (1H)-one

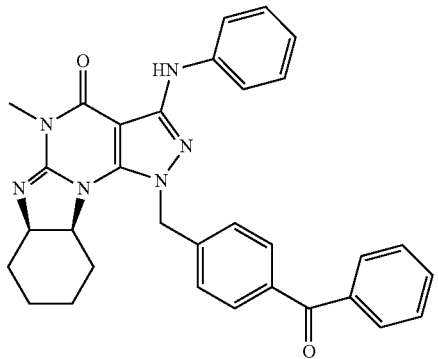 [SMILES: CN1C(=O)c2c(Nc3ccccc3)nn(Cc3ccc(C(=O)c4ccccc4)cc3)c2N2C1=N[C@@H]1CCCC[C@@H]12]

(a) 7-(4-Methoxybenzyl)-5-methyl-3-(phenylamino)-1H-pyrazolo[3,4-d]pyrimidine-4,6(5H,7H)-dione Phenyl isothiocyanate (3.9 mL, 32.7 mmol) is added to a suspension of 6-hydrazinyl-1-(4-methoxybenzyl)-3-methyl-pyrimidine-2,4(1H,3H)-dione (0.45 g, 1.6 mmol) in DMF (12 mL). The reaction mixture is heated at 120° C. for 40 hours, and then evaporated to remove solvent under reduced pressure. The residue is washed with hexanes, and then treated with MeOH (125 mL), and stored at −15° C. for 2 days to give a crystalline solid. The solid is recrystallized from CH$_3$OH-EtOAc to afford 2.5 g product (Yield: 61%).
$^1$H NMR (400 MHz, DMSO-d$_6$) δ3.21 (s, 3H), 3.73 (s, 3H), 5.01 (s, 2H), 6.88-7.36 (m, 9H). MS (FAB) m/z 378.3 [M+H]$^+$.

(b) 5-Methyl-3-(phenylamino)-1H-pyrazolo[3,4-d]pyrimidine-4,6(5H,7H)-dione

AlCl$_3$ (0.733 g, 5.50 mmol) is added to a solution of 7-(4-methoxybenzyl)-5-methyl-3-(phenylamino)-1H-pyrazolo[3,4-d]pyrimidine-4,6(5H,7H)-dione (0.692 g, 1.83 mmol) and anisole (40 μL, 0.367 mmol) in 1,2-dichloroethane (10 mL) under argon. The reaction mixture is stirred at room temperature for 30 min, and then quenched with water with cooling. The resulting suspension is filtered through a layer of celite and the celite is washed with MeOH (20 mL). The product is eluted from the celite with a large amount of THF. The THF eluent is evaporated to afford 0.47 g of product (Yield: 99%). MS (FAB) m/z 258.2 [M+H]$^+$.

(c) 6-Chloro-5-methyl-3-(phenylamino)-1H-pyrazolo[3,4-d]pyrimidin-4(5H)-one 5-methyl-3-(phenylamino)-1H-pyrazolo[3,4-d]pyrimidine-4,6(5H,7H)-dione (450 mg, 1.75 mmol) is refluxed in POCl$_3$ (20 mL) for 60 hours, and the mixture is evaporated to dryness. The residue is purified by silica gel flash chromatography to give 122 mg product as white solids and 207 mg starting material is recovered (Yield: 47%). MS (FAB) m/z 276.1 [M+H]$^+$.

(d) 6-((1R*,2R*)-2-Hydroxycyclohexylamino)-5-methyl-3-(phenylamino)-1H-pyrazolo[3,4-d]pyrimidin-4(5H)-one A solution of 6-chloro-5-methyl-3-(phenylamino)-1H-pyrazolo[3,4-d]pyrimidin-4(514)-one (75.8 mg, 0.275 mmol), trans-2-amino-cyclohexanol hydrochloride (83.4 mg, 0.55 mmol) and DIPEA (144 μL, 0.825 mmol) in DMF (3 mL) is heated at 110° C. overnight. The reaction mixture is evaporated to remove DMF under reduced pressure. The residue is then purified by chromatography to give 63.1 mg product (Yield: 64.7%). MS (ESI) m/z 355.0 [M+H]$^+$.

(e) Cis-(6aR*,10aS*)-5,6a,7,8,9,10,10a-heptahydro-5-methyl-3-(phenylamino)cyclohex[4,5]imidazo[1,2-a]pyrazolo[4,3-e]pyrimidin-4(1H)-one 2.0 M solution of thionyl chloride in CH$_2$Cl$_2$ (267 μL, 0.534 mmol) is added to a solution of 6-((1R*,2R*)-2-hydroxycyclohexylamino)-5-methyl-3-(phenylamino)-1H-pyrazolo[3,4-d]pyrimidin-4(5H)-one (63.1 mg, 0.178 mmol) in CH$_2$Cl$_2$ (6 mL) and THF (4 mL). The reaction mixture is stirred at r.t. overnight, and then quenched with 100 μL of 28% NH$_4$OH. The resulting mixture is concentrated and purified by chromatography to give 25 mg product as white solids (Yield: 42%). MS (ESI) m/z 337.1 [M+H]⁺.

(f) Cis-(6aR*,10aS*)-1-(4-Benzoylbenzyl)-5,6a,7,8,
9,10,10a-heptahydro-5-methyl-3-(phenylamino)cyclohex[4,5]imidazo[1,2-a]pyrazolo[4,3-e]pyrimidin-4(1H)-one A mixture of Cis-(6aR*,10aS*)-5,6a,7,8,9,10,10a-heptahydro-5-methyl-3-(phenylamino)cyclohex[4,5]imidazo[1,2-a]pyrazolo[4,3-e]pyrimidin-4(1H)-one (7.1 mg, 0.021 mmol), 4-benzoylbenzyl bromide (5.8 mg, 0.021 mmol), and K₂CO₃ (2.92 mg, 0.021 mmol) in DMF (1 mL) is stirred at room temperature overnight under argon. The reaction mixture is purified by a semi-preparative HPLC to give 3.5 mg of the final product (Yield: 31%). MS (ESI) m/z 531.1 [M+H]⁺.

Example 3

3-Benzyl-2-(biphenyl-4-ylmethyl)-7,8-dihydro-5,7,7-trimethyl-[2H]-imidazo-[1,2-a]pyrazolo[4,3-e]pyrimidin-4(5H)-one

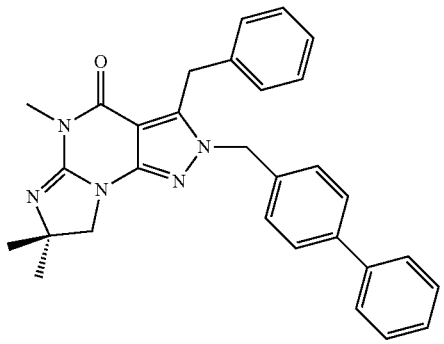

(a) 6-(2-(Biphenyl-4-ylmethylene)hydrazinyl)-1-(4-methoxybenzyl)-3-methylpyrimidine-2,4(1H,3H)-dione A solution of 4-phenylbenzaldehyde (395 mg, 2.17 mmol) in EtOAc is slowly added into a dry ice cooled slurry of 6-hydrazinyl-1-(4-methoxybenzyl)-3-methylpyrimidine-2,4 (1H,3H)-dione (200 mg, 0.724 mmol) in EtOAc. After the addition, the reaction mixture is stirred at room temperature for 2 hours. The solvent is evaporated under reduced pressure, and the residue is triturated with MeOH, followed by filtration to give 256 mg product as pale yellow solids (Yield: 80.3%). ¹H NMR (400 MHz, DMSO-d₆) δ 3.17 (s, 3H), 3.71 (s, 3H), 5.22 (s, 2H), 5.59 (s, 1H), 6.91 and 7.21 (AB, J=7.2 Hz, 4H), 7.37-7.81 (m, 9H), 8.36 (s, 1H), 10.67 (s, 1H). MS (FAB) m/z 441.4 [M+H]⁺.

(b) 3-Benzyl-2-(biphenyl-4-ylmethyl)-7-(4-methoxybenzyl)-5-methyl-2H-pyrazolo[3,4-d]pyrimidine-4,6(5H,7H)-dione Acetic acid (4.4 mL) is added in to a solution of 6-(2-(Biphenyl-4-ylmethylene)hydrazinyl)-1-(4-methoxybenzyl)-3-methylpyrimidine-2,4(1H,3H)-dione (3.2 g, 7.26 mmol) in DMF (50 mL) and BuᵗOH (25 mL) at 50° C.

Piperidine (8.7 mL) is mixed with a solution of 2-phenylacetaldehyde (8.5 mL, 72.6 mmol) in DMF (20 mL), and the resulting greenish solution is added in to the above solution. The reaction mixture is stirred at 40-45° C. for 36 hours under argon, and the solvent is evaporated under high vacuum. The residue is treated with MeOH (200 mL) to precipitate out 1.23 g product as sandy solids (Yield: 31.4%). MS (FAB) m/z 543.4 [M+H]⁺.

(c) 3-Benzyl-2-(biphenyl-4-ylmethyl)-5-methyl-2H-pyrazolo[3,4-d]pyrimidine-4,6(5H,7H)-dione A solution of ammonium cerium (IV) nitrate (204 mg, 0.371 mmol) in water (0.6 mL) is added to a solution of 3-benzyl-2-(biphenyl-4-ylmethyl)-7-(4-methoxybenzyl)-5-methyl-2H-pyrazolo[3,4-d]pyrimidine-4,6(5H,7H)-dione (40.3 mg, 0.0743 mmol) in THF (2 mL). The resulting orange solution is stirred at room temperature overnight. Another batch of CAN (204 mg, 0.371 mmol) is added and the mixture is stirred for 3 hours, and then the third batch of CAN (204 mg) is added, and the mixture is stirred at r.t. overnight. The reaction mixture is evaporated to dryness. The residue is treated with brine, and extracted with methylene chloride five times. The organic phase is combined and concentrated. The residue is purified by chromatography to give 11.6 mg product as white solids (Yield: 36.9%). ¹H NMR (400 MHz, acetone-d₆) δ 3.27 (s, 3H), 4.51 (s, 2H), 5.33 (s, 2H), 7.13-7.62 (m, 14H), 10.26 (s, 1H). MS (FAB) m/z 423.2 [M+H]⁺.

(d) 3-Benzyl-2-(biphenyl-4-ylmethyl)-6-chloro-5-methyl-2H-pyrazolo[3,4-d]pyrimidin-4(5H)-one 3-benzyl-2-(biphenyl-4-ylmethyl)-5-methyl-2H-pyrazolo[3,4-d]pyrimidine-4,6(5H,7H)-dione (10 mg, 0.024 mmol) is refluxed in POCl₃ (10 mL) for 4 days, and then the mixture is evaporated to dryness. The residue is purified by silica gel flash chromatography to give 10.4 mg product as white solids (Yield: 100%). MS (FAB) m/z 441.2 [M+H]⁺.

(e) 3-Benzyl-2-(biphenyl-4-ylmethyl)-6-(1-hydroxy-2-methylpropan-2-ylimino)-5-methyl-6,7-dihydro-2H-pyrazolo[3,4-d]pyrimidin-4(5H)-one A solution of 3-Benzyl-2-(biphenyl-4-ylmethyl)-6-chloro-5-methyl-2H-pyrazolo[3,4-d]pyrimidin-4(5H)-one (9.5 mg, 0.022 mmol) and 2-amino-2-methyl-1-propanol (21 μL, 0.22 mmol) in DMF (2 mL) is heated at 110° C. overnight. The reaction mixture is then purified by chromatography to give 5.5 mg product (Yield: 52%). MS (FAB) m/z 494.4 [M+H]⁺.

(f) 3-Benzyl-2-(biphenyl-4-ylmethyl)-7,8-dihydro-5,7,7-trimethyl-[2H]-imidazo-[1,2-a]pyrazolo[4,3-e]pyrimidin-4(5H)-one A 2.0 M solution of thionyl chloride (25 μL, 0.050 mmol) in CH₂Cl₂ is added into a solution of 3-benzyl-2-(biphenyl-4-ylmethyl)-6-(1-hydroxy-2-methylpropan-2-ylimino)-5-methyl-6,7-dihydro-2H-pyrazolo[3,4-d]pyrimidin-4(5H)-one (5.0 mg, 0.010 mmol) in methylene chloride (1 mL). The reaction mixture is stirred at r.t. overnight, and then quenched with 5% NaHCO₃. The resulting mixture is purified by chromatography to give 3.2 mg of the final product (Yield: 67%). MS (FAB) m/z 476.4 [M+H]⁺.

Example 4

1-(Biphenyl-4-ylmethyl)-7,8-dihydro-5,7,7-trimethyl-3-(phenylamino)[1H]-imidazo-[1,2-a]pyrazolo[4,3-e]pyrimidin-4(5H)-one

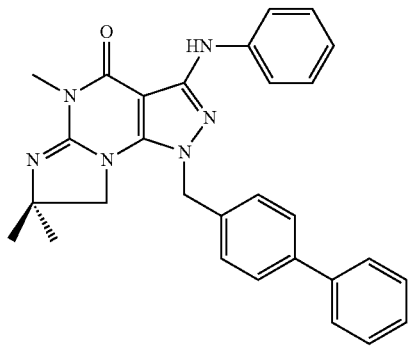

The synthesis method is analogous to example 2 wherein 2-amino-2-methyl-1-propanol is added in step (d) instead of trans-2-amino-cyclohexanol hydrochloride; and p-biphenyl-methyl bromide is added in step (f) instead of benzoylbenzyl bromide.

Example 5

1-(4-(1,2,3-thiadiazol-4-yl)benzyl)-7,8-dihydro-5,7,7-trimethyl-3-(phenylamino)-[1H]-imidazo-[1,2-a]pyrazolo[4,3-e]pyrimidin-4(5H)-one

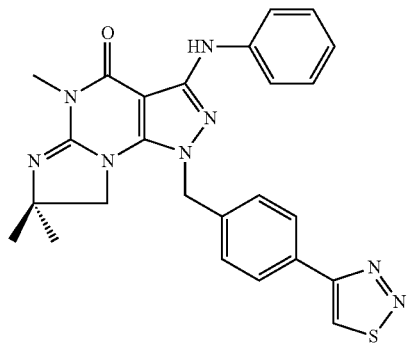

The synthesis method is analogous to example 2 wherein 2-amino-2-methyl-1-propanol is added in step (d) instead of trans-2-amino-cyclohexanol hydrochloride; and 4-(1,2,3-thiadiazol-4yl)benzyl bromide is added in step (f) instead of benzoylbenzyl bromide.

Example 6

1-(Biphenyl-4-ylmethyl)-3-((biphenyl-4-ylmethyl)(phenyl)amino)-7,8-dihydro-5,7,7-trimethyl-[1H]-imidazo-[1,2-a]pyrazolo[4,3-e]pyrimidin-4(5H)-one

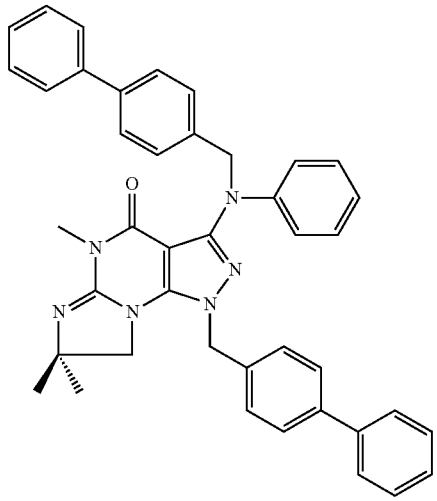

The synthesis method is analogous to example 2 wherein 2-amino-2-methyl-1-propanol is added in step (d) instead of trans-2-amino-cyclohexanol hydrochloride; and p-biphenyl-methyl bromide is added in step (f) instead of benzoylbenzyl bromide.

Example 7

Cis-(6aR*,10aS*)-5,6a,7,8,9,10,10a-heptahydro-5-methyl-3-(phenylamino)-1-(4-(pyridin-2yl)benzyl)-cyclohex[4,5]imidazo[1,2-a]pyrazolo[4,3-e]pyrimidin-4-(1H)-one

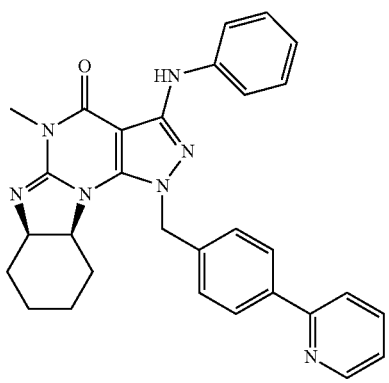 [SMILES: CN1C(=O)c2c(Nc3ccccc3)nn(Cc3ccc(-c4ccccn4)cc3)c2N2C1=N[C@@H]1CCCC[C@@H]12]

The synthesis method is analogous to example 2 wherein 2-(4-(bromomethyl)phenyl)pyridine is added in step (f) instead of benzoylbenzyl bromide.

Example 8

Cis-(6aR*,10aS*)-2-(4-(Pyridin-2yl)benzyl)-5,6a,7,8,9,10,10a-heptahydro-5-methyl-3-(phenylamino)cyclohex[4,5]imidazo[1,2-a]pyrazolo[4,3-e]pyrimidin-4(2H)-one

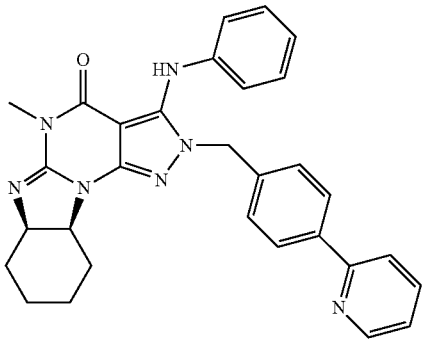 [SMILES: CN1C(=O)c2c(nn(Cc3ccc(-c4ccccn4)cc3)c2Nc2ccccc2)N2C1=N[C@@H]1CCCC[C@@H]12]

The synthesis method is analogous to example 2 wherein 4-pyrid-2-ylbenzyl bromide is added in step (f) instead of benzoylbenzyl bromide.

Example 9

Cis-(6aR*,10aS*)-3-(Benzyl)-5,6a,7,8,9,10,10a-heptahydro-5-methyl-2-(4-(1,2,3-thiadiazol-4-yl)benzyl)-cyclohex[4,5]imidazo[1,2-a]pyrazolo[4,3-e]pyrimidin-4(2H)-one

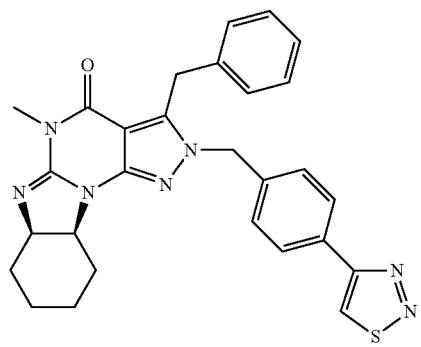 [SMILES: CN1C(=O)c2c(nn(Cc3ccc(-c4csnn4)cc3)c2Cc2ccccc2)N2C1=N[C@@H]1CCCC[C@@H]12]

The synthesis method is analogous to example 3 wherein 4-(1,2,3-thiadiazol-4yl)benzaldehyde and DMF is added in step (a) instead of 4-phenylbenzaldehyde and heated overnight; and trans-2-amino-cyclohexanol hydrochloride is added in step (e) instead of 2-amino-2-methyl-1-propanol.

Example 10

Cis-(6aR*,10aS*)-3-(Benzyl)-2-(4-Biphenyl-4-ylmethyl)-5,6a,7,8,9,10,10a-heptahydro-5-methyl-cyclohex[4,5]imidazo[1,2-a]pyrazolo[4,3-e]pyrimidin-4(2H)-one

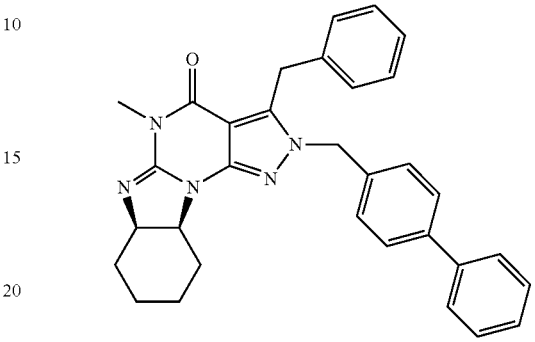

The synthesis method is analogous to example, 3 wherein trans-2-amino-cyclohexanol hydrochloride is added in step (e) instead of 2-amino-2-methyl-1-propanol.

Example 11

(R)-3-(Benzyl)-2-(biphenyl-4-ylmethyl)-7,8-dihydro-7-isopropyl-5-methyl-[2H]-imidazo-[1,2-a]pyrazolo[4,3-e]pyrimidin-4(5H)-one

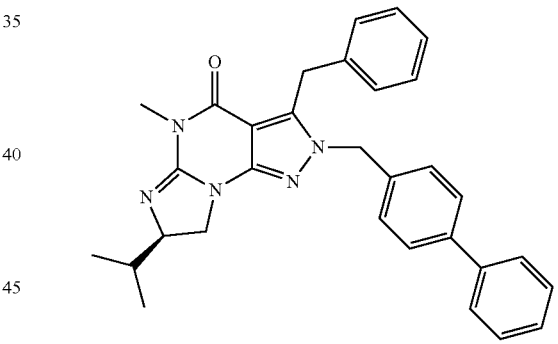

The synthesis method is analogous to example 3 wherein (R)-2-amino-3-methybutan-1-ol is added in step (e) instead of 2-amino-2-methyl-1-propanol.

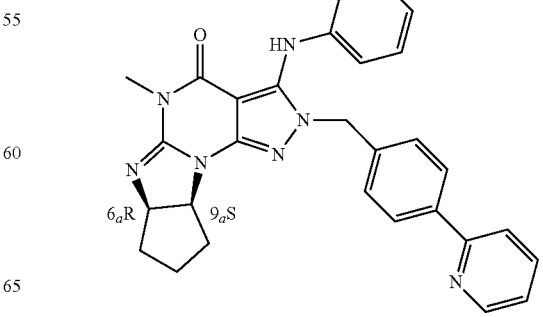

Example 12

(6aR,9aS)-5,6a,7,8,9,9a-hexahydro-5-methyl-3-(phenylamino)-2-(4-(pyridin-2-yl)-benzyl)-cyclopent[4,5]imidazo[1,2-a]-pyrazolo[4,3-e]pyrimidin-4(2H)-one The synthesis method is analogous to example 2 wherein (1R,2R)-2-amino-cyclopentanol is added in step (d) instead of trans-2-amino-cyclohexanol hydrochloride; and 2-(4-(bromomethyl)phenyl)pyridine is added in step (f) instead of benzoylbenzyl bromide.

Example 13

(6aR,9aS)-5,6a,7,8,9,9a-hexahydro-5-methyl-3-(phenylamino)-1-(4-Pyridin-2yl)-benzyl)-cyclopent[4,5]imidazo[1,2-a]pyrazolo[4,3-e]pyrimidin-4(1H)-one

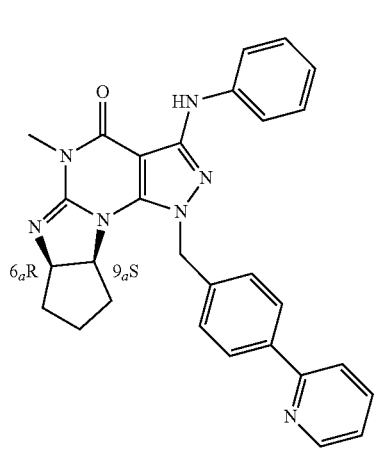 [SMILES: CN1C(=O)c2c(Nc3ccccc3)nn(Cc3ccc(-c4ccccn4)cc3)c2N2C1=N[C@@H]1CCC[C@@H]12]

The synthesis method is analogous to example 2 wherein (1R,2R)-2-amino-cyclopentanol is added in step (d) instead of trans-2-amino-cyclohexanol hydrochloride; and 4-pyrid-2-ylbenzyl bromide is added in step (f) instead of benzoylbenzyl bromide.

Example 14

(6aR,9aS)-3-(benzylamino)-5,6a,7,8,9,9a-hexahydro-5-methyl-2-(4-Pyridin-2yl)-benzyl)-cyclopent[4,5]imidazo[1,2-a]pyrazolo[4,3-e]pyrimidin-4(2H)-one

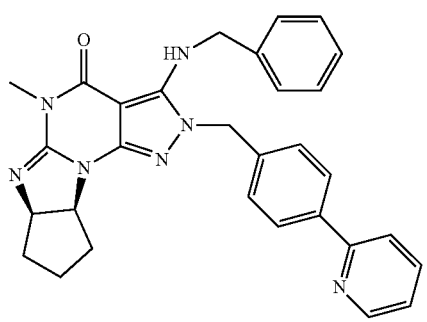 [SMILES: CN1C(=O)c2c(nn(Cc3ccc(-c4ccccn4)cc3)c2NCc2ccccc2)N2C1=N[C@@H]1CCC[C@@H]12]

The synthesis method is analogous to example 2 wherein benzyl isothiocyanate is added in step (a) instead of phenyl isothiocyanate; (1R,2R)-2-amino-cyclopentanol is added in step (d) instead of trans-2-amino-cyclohexanol hydrochloride; and 4-pyrid-2-ylbenzyl bromide is added in step (f) instead of benzoylbenzyl bromide.

Example 15

(6aR,9aS)-3-(phenylamino)-5,6a,7,8,9,9a-hexahydro-5-methyl-2-(biphenyl-4-ylmethyl)-cyclopent[4,5]imidazo[1,2-a]pyrazolo[4,3-e]pyrimidin-4(2H)-one

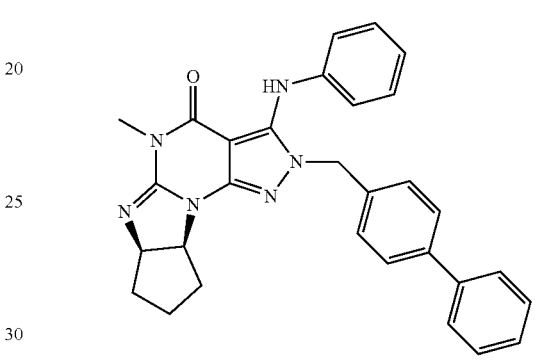

The synthesis method is analogous to example 2 wherein (1R,2R)-2-amino-cyclopentanol is added in step (d) instead of trans-2-amino-cyclohexanol hydrochloride; and 4-(bromomethyl)biphenyl is added in step (f) instead of benzoylbenzyl bromide.

Example 16

2-(Biphenyl-4-ylmethyl)-7,8,9-trihydro-5,8,8-trimethyl-3-(phenylamino)-[2H]-pyrimido-[1,2-a]pyrazolo[4,3-e]pyrimidin-4(5H)-one

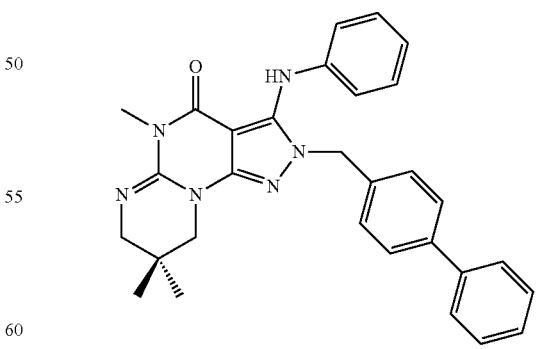

The synthesis method is analogous to example 2 wherein 3-amino-2,2-dimethyl-1-propanol is added in step (d) instead of trans-2-amino-cyclohexanol hydrochloride; and 4-(bromomethyl)biphenyl is added in step (f) instead of benzoylbenzyl bromide.

Example 17

(7R)-2-(Biphenyl-4-ylmethyl)-7,8-dihydro-5,7-dimethyl-3-(phenylamino)-[2H]-imidazo-[1,2-a]pyrazolo[4,3-e]pyrimidin-4(5H)-one

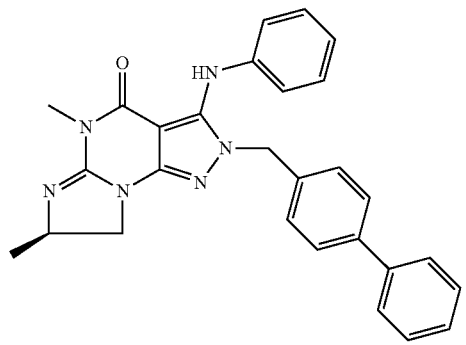 [SMILES: C[C@@H]1CN2C(=N1)N(C)C(=O)c1c2nn(Cc2ccc(-c3ccccc3)cc2)c1Nc1ccccc1]

The synthesis method is analogous to example 2 wherein (R)-2-aminoprop-1-ol is added in step (d) instead of trans-2-amino-cyclohexanol hydrochloride; and 4-(bromomethyl)biphenyl is added in step (f) instead of benzoylbenzyl bromide.

Example 18

(8R)-2-(Biphenyl-4-ylmethyl)-7,8-dihydro-5,8-dimethyl-3-(phenylamino)-[2H]-imidazo-[1,2-a]pyrazolo[4,3-e]pyrimidin-4(5H)-one

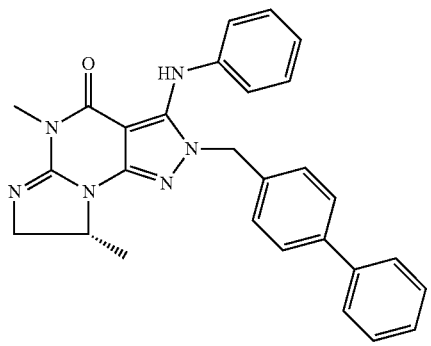 [SMILES: C[C@@H]1CN=C2N(C)C(=O)c3c(nn(Cc4ccc(-c5ccccc5)cc4)c3Nc3ccccc3)N21]

The synthesis method is analogous to example 2 wherein (R)-1-aminopropan-2-ol is added in step (d) instead of trans-2-amino-cyclohexanol hydrochloride; and 4-(bromomethyl)biphenyl is added in step (f) instead of benzoylbenzyl bromide.

Example 19

(7R)-2-(Biphenyl-4-ylmethyl)-7,8-dihydro-3-(phenylamino)-5-methyl-7-(1-methylethyl)-[2H]-imidazo-[1,2-a]pyrazolo[4,3-e]pyrimidin-4(5H)-one

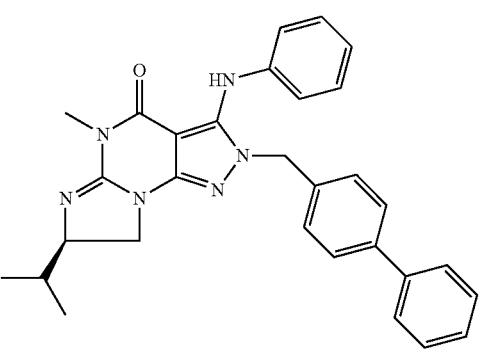 [SMILES: CC(C)[C@@H]1CN2C(=N1)N(C)C(=O)c1c2nn(Cc2ccc(-c3ccccc3)cc2)c1Nc1ccccc1]

The synthesis method is analogous to example 2 wherein (R)-2-amino-3-methylbutan-1-ol is added in step (d) instead of trans-2-amino-cyclohexanol hydrochloride; and 4-(bromomethyl)biphenyl is added in step (f) instead of benzoylbenzyl bromide.

Example 20

(6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one

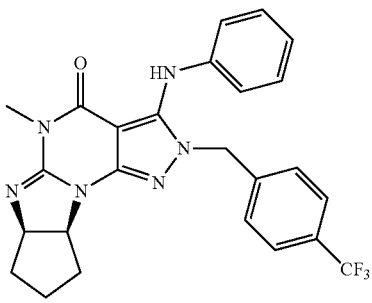 [SMILES: CN1C(=O)c2c(nn(Cc3ccc(C(F)(F)F)cc3)c2Nc2ccccc2)N2C1=N[C@@H]1CCC[C@@H]12]

The synthesis method is analogous to example 2 wherein (1R,2R)-2-amino-cyclopentanol is added in step (d) instead of trans-2-amino-cyclohexanol hydrochloride; and p-trifluoromethylbenzyl bromide is added in step (f) instead of benzoylbenzyl bromide.

Example 21

(6aR,9aS)-3-(phenylamino)-5,6a,7,8,9,9a-hexa-hydro-5-methyl-2-((6-trifluoromethyl)-pyridin-3-yl)methyl)-cyclopent[4,5]imidazo[1,2-a]pyrazolo[4,3-e]pyrimidin-4(2H)-one

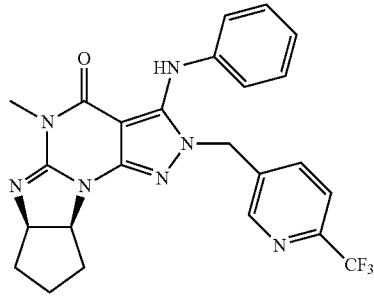 [SMILES: CN1C(=O)c2c(nn(Cc3ccc(C(F)(F)F)nc3)c2Nc2ccccc2)N2C1=N[C@@H]1CCC[C@@H]12]

The synthesis method is analogous to example 2 wherein (1R,2R)-2-amino-cyclopentanol is added in step (d) instead of trans-2-amino-cyclohexanol hydrochloride; and 5-(bromomethyl)-2-(trifluoromethyl)pyridine is added in step (f) instead of benzoylbenzyl bromide.

Example 22

(6aR,9aS)-3-(phenylamino)-5,6a,7,8,9,9a-hexa-hydro-5-methyl-2-(3-fluoro-4-(trifluoromethyl)-benzyl)-cyclopent[4,5]imidazo[1,2-a]pyrazolo[4,3-e]pyrimidin-4(2H)-one

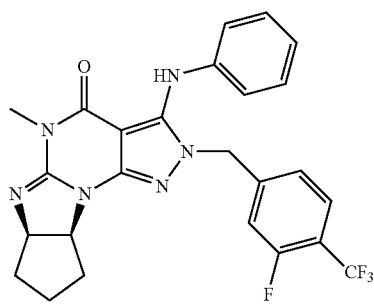 [SMILES: CN1C(=O)c2c(nn(Cc3ccc(C(F)(F)F)c(F)c3)c2Nc2ccccc2)N2C1=N[C@@H]1CCC[C@@H]12]

The synthesis method is analogous to example 2 wherein (1R,2R)-2-amino-cyclopentanol is added in step (d) instead of trans-2-amino-cyclohexanol hydrochloride; and 3-fluoro-4-trifluoromethyl-benzyl bromide is added in step (f) instead of benzoylbenzyl bromide.

Example 23

(6aR,9aS)-3-(phenylamino)-5,6a,7,8,9,9a-hexa-hydro-5-methyl-2-(4-methylsulfonyl-benzyl)-cyclopent[4,5]imidazo[1,2-a]pyrazolo[4,3-e]pyrimidin-4(2M-one

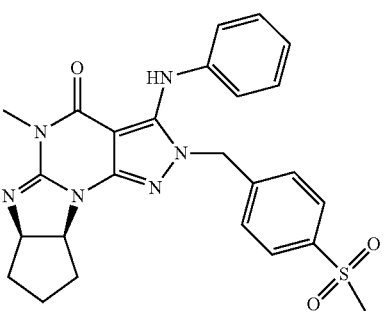 [SMILES: CN1C(=O)c2c(nn(Cc3ccc(S(C)(=O)=O)cc3)c2Nc2ccccc2)N2C1=N[C@@H]1CCC[C@@H]12]

The synthesis method is analogous to example 2 wherein (1R,2R)-2-amino-cyclopentanol is added in step (d) instead of trans-2-amino-cyclohexanol hydrochloride; and p-methylsulfonyl-benzyl bromide is added in step (f) instead of benzoylbenzyl bromide.

Example 24

Measurement of PDE1B Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Amp, is indicative of inhibition of PDE activity. $IC_{50}$ values The compounds of Examples 1-14 have $IC_{50}$ values of less than 1 μM in this assay, generally less than 10 nM.

The invention claimed is:

1. A method for the treatment of a circulatory or cardiovascular disorder selected from cerebrovascular disease, stroke, congestive heart disease, hypertension, pulmonary hypertension, and sexual dysfunction, comprising administering to a patient in need thereof, a compound of Formula I:

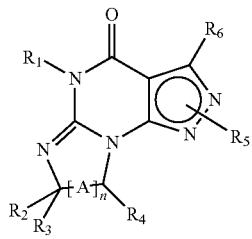

wherein
i. $R_1$ is H or $C_{1-4}$ alkyl;
ii. $R_4$ is H or $C_{1-4}$ alkyl and $R_2$ and $R_3$ are, independently, H or $C_{1-4}$ alkyl, aryl, heteroaryl, (optionally hetero)arylalkoxy, or (optionally hetero)arylalkyl; or $R_2$ is H and $R_3$ and $R_4$ together form a di-, tri- or tetramethylene bridge
iii. $R_5$ is a substituted heteroarylalkyl, or $R_5$ is attached to one of the nitrogen atoms on the pyrazolo portion of Formula I and is a moiety of Formula A

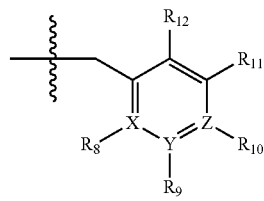

wherein X, Y and Z are, independently, N or C; $R_8$, $R_9$, $R_{11}$ and $R_{12}$ are independently H or halogen; and $R_{10}$ is halogen, alkyl, cycloalkyl, haloalkyl, aryl, heteroaryl, or thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present;
iv. $R_6$ is H, alkyl, aryl, heteroaryl, arylalkyl, arylamino, heterarylamino, N,N-dialkylamino, N,N-diarylamino, or N-aryl-N-(arylakyl)amino; and
v. n=0 or 1;
vi. when n=1, A is —C($R_{13}R_{14}$)— wherein $R_{13}$ and $R_{14}$ are independently H or $C_{1-4}$ alkyl, aryl, heteroaryl, heteroarylalkoxy, arylalkoxy, heteroarylalkyl or arylalkyl,
in free, pharmaceutically acceptable salt or physiologically hydrolysable and acceptable ester prodrug form.

2. The method according to claim 1, wherein said compound is a compound of Formula IV

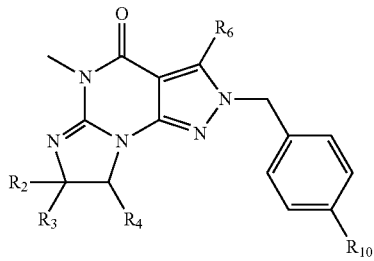

wherein:
$R_2$ is H and $R_3$ and $R_4$ together form a tri- or tetramethylene bridge;
$R_6$ is phenylamine or benzylamino;
$R_{10}$ is phenyl, pyridyl, or thiadiazolyl, wherein phenyl is optionally substituted with $C_{1-4}$ alkyl, halogen, halo$C_{1-4}$ alkyl, hydroxy, carboxy or an additional aryl or heteroaryl; and pyridyl or thiadiazolyl is optionally substituted with $C_{1-4}$ alkyl, halogen, halo$C_{1-4}$alkyl, hydroxy or carboxy; in free, salt or physiologically hydrolysable and acceptable ester prodrug form.

3. The method according to claim 2, wherein $R_2$ is H and $R_3$ and $R_4$ together form a tri- or tetra-methylene bridge wherein the carbons carrying $R_3$ and $R_4$ have the R and S configuration respectively, in free, pharmaceutically acceptable salt or physiologically hydrolysable and acceptable ester prodrug form.

4. The method according to claim 2, wherein $R_2$ is U and $R_3$ and $R_4$ together form a tri-methylene bridge wherein the carbons carrying $R_3$ and $R_4$ have the R and S configuration respectively, in free, pharmaceutically acceptable salt or physiologically hydrolysable and acceptable ester prodrug form.

5. The method according to claim 4, wherein $R_{10}$ is phenyl optionally substituted with $C_{1-4}$ alkyl, halogen, halo$C_{1-4}$ alkyl, hydroxy, carboxy or an additional aryl or heteroaryl, in free, pharmaceutically acceptable salt or physiologically hydrolysable and acceptable ester prodrug form.

6. The method according to claim 4, wherein $R_{10}$ is pyrid-2-yl er 1,2,3-thiadiazol-4-yl, optionally substituted with $C_{1-4}$alkyl, halogen, halo$C_{1-4}$alkyl, hydroxy, carboxy or an additional aryl or heteroaryl, in free, pharmaceutically acceptable salt or physiologically hydrolysable and acceptable ester prodrug form.

7. The method according to claim 4, wherein $R_6$ is phenylamino optionally substituted with $C_{1-4}$ alkyl, halogen, halo$C_{1-4}$alkyl, hydroxy, carboxy or an additional aryl or heteroaryl, in free, pharmaceutically acceptable salt or physiologically hydrolysable and acceptable ester prodrug form.

8. The method according to claim 4, wherein $R_{10}$ is pyridyl substituted with $C_{1-4}$ alkyl, halogen, halo$C_{1-4}$alkyl, hydroxy or carboxy, in free, pharmaceutically acceptable salt or physiological hydrolysable and acceptable ester prodrug form.

9. The method according to claim 8, wherein $R_6$ is phenylamino, ha free, pharmaceutically acceptable salt or physiological hydrolysable and acceptable ester prodrug form.

10. The method according to claim 2, wherein said compound is selected from any of the following:

Cis-(6aR*,10aS*)-1-(4-Benzoylbenzyl)-5,6a,7,8,9,10,10a-heptahydro-5-methyl-3-(phenylamino)cyclohex[4,5]imidazo[1,2-a]pyrazolo[4,3-e]pyrimidin-4(1H-one;

Cis-(6aR*,10aS*)-5,6a,7,8,9,10,10a-heptahydro-5-methyl-3-(phenylamino)-1-(4-(pyridin-2-yl)benzyl)benzyl)-cyclohex[4,5]imidazo[1,2-a]pyrazolo[4,3-e]pyrimidin-4-(1H)-one;

Cis-(6aR*,10aS*)-2-(4-(Pyridin-2-yl)benzyl)-5,6a,7,8,9,10,10a-heptahydro-5-methyl-3-(phenylamino)cyclohex[4,5]imidazo[1,2-a]pyrazolo[4,3-e]pyrimidin-4(2H)-one;

Cis-(6aR*,10aS*)-3-(Benzyl)-5.6a,7,8,9,10,10a-heptahydro-5-methyl-2-(4-(1,2,3-thiadiazol-4-yl)benzyl)-cyclohex[4,5]imidazo[1,2-a]pyrazolo[4,3-e]pyrimidin-4(2H)-one;

Cis-(6aR*,10aS*)-3-(Benzyl)-2-(4-Biphenyl-4-ylmethyl)-5,6a,7,8,9,10,10a-heptahydro-5-methyl-cyclohex[4,5]imidazo[1,2-a]pyrazolo[4,3-e]pyrimidin-4(2H)-one;

(6aR,9aS)-5,6a,7,8,9,9a-hexahydro-5-methyl-3-(phenylamino)-2-(4-(pyridin-2-yl)-benzyl)-cyclopent[4,5]imidazo[1,2-a]pyrazolo[4,3-e]pyrimidin-4(2H)-one;

(6aR,9aS)-5,6a,7,8,9,9a-hexahydro-5-methyl-3-(phenylamino)-1-(4-Pyridin-2-yl)-benzyl)-cyclopent[4,5]imidazo[1,2-a]pyrazolo[4,3-e]pyrimidin-4(1H)-one;

(6aR,9aS)-3-(benzylamino)-5,6a,7,8,9,9a-hexahydro-5-methyl-2-(4-Pyridin-2-yl)-benzyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-(biphenyl-4-ylmethyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-((6-trifluoromethyl)-pyridin-3-yl)methyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-(3-fluoro-4-(trifluoromethyl)-benzyl)-cyclopent[4,5]imidazo[1,2-a]pyrazolo[4,3-e]pyrimidin-4(2H)-one; and (6aR,9aS)-3-(phenylamino)-5,6a,7,8,9,9a-hexahydro-5-methyl-2-(4-methylsulfonyl-benzyl)-cyclopent[4,5]imidazo[1,2-a]pyrazolo[4,3-e]pyrimidin-4(2H)-one;

in free, pharmaceutically acceptable salt form, or in pure enantiomeric form.

11. The method according to claim 2, wherein said compound is (6aR,9aS)-5,6a,7,8,9,9a-hexahydro-5-methyl-3-(phenylamino)-2-(4-(pyridin-2-yl)-benzyl)-cyclopent[4,5]imidazo[1,2-a]pyrazolo[4,3-e]pyrimidin-4(2H)-one in free, pharmaceutically acceptable salt or pure enantiomeric form.

12. The method according to claim 2, wherein said compound is (6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-onein free, pharmaceutically acceptable salt or pure enantiomeric form.

13. The method according to claim 1, wherein the compound is a compound of Formula I

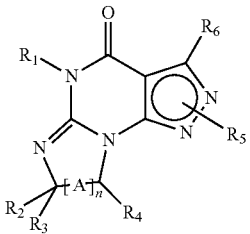

i. $R_1$ is H or $C_{1-4}$ alkyl;
ii. $R_4$ is H and at least one of $R_2$ and $R_3$ is lower alkyl, such that when the carbon carrying $R_3$ is chiral, it has the R configuration;
iii. $R_5$ is a substituted heteroarylalkyl, or $R_5$ is attached to one of the nitrogen atoms on the pyrazolo portion of Formula I and is a moiety of Formula A

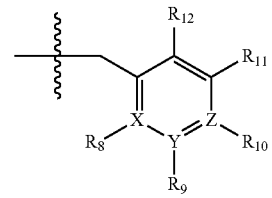

wherein X, Y and Z are, independently, N or C; $R_8$, $R_9$, $R_{11}$ and $R_{12}$ are independently H or halogen; and $R_{10}$ is halogen, alkyl, cycloalkyl, haloalkyl, aryl, heteroaryl, or thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present;
iv. $R_6$ is H, alkyl, aryl, heteroaryl, arylalkyl, arylamino, heterarylamino, N,N-dialkylamino, N,N-diarylamino, or N-aryl-N(arylalkyl)amino; and
v. n=0 or 1; when n=1, A is —C($R_{13}R_{14}$)— wherein $R_{13}$ and $R_{14}$, are, independently, H or $C_{1-4}$ alkyl, aryl, heteroaryl, heteroarylalkoxy, arylalkoxy, heteroarylalkyl or arylalkyl, wherein
  aryl is optionally substituted with $C_{1-4}$alkyl, halogen, halo$C_{1-4}$alkyl, hydroxy, carboxy or an additional aryl or heteroaryl; and
  heteroaryl is optionally substituted with $C_1$-4alkyl, halogen, halo$C_{1-4}$alkyl, hydroxy or carboxy;
in free, salt or physiological hydrolysable and acceptable ester prodrug form.

14. The method according to claim 1 which is a compound of Formula II

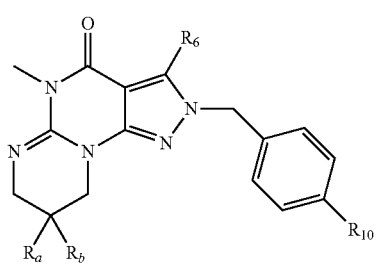

Formula II wherein
$R_a$ and $R_b$ are, independently, H or $C_{1-4}$ alkyl;
$R_6$ is phenylamino;
$R_{10}$ is phenyl, pyridyl, or thiadiazolyl;
in free or salt form.

15. The method according to claim 1 which is a compound of Formula III:

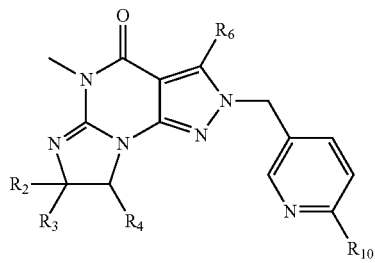

Formula III wherein
at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino;
$R_{10}$ is haloalkyl, phenyl, pyridyl, or thiadiazolyl;
in free or salt form.

16. The method according to claim 1, which is a compound of Formula IV

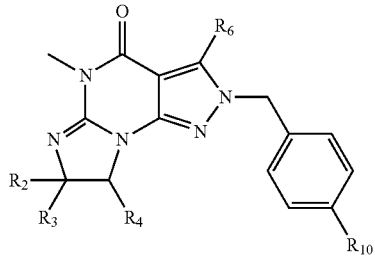

Formula IV wherein
at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino;
$R_{10}$ is phenyl, pyridyl, or thiadiazolyl;
wherein
phenyl is optionally substituted with $C_{1-4}$alkyl, halogen, halo$C_{1-4}$alkyl, hydroxy, carboxy or an additional aryl or heteroaryl; and
pyridyl and thiadiazolyl is optionally substituted with $C_{1-4}$alkyl, halogen, halo$C_{1-4}$alkyl, hydroxy or carboxy;
in free or salt form.

17. The method according to claim 1 of formula Ia

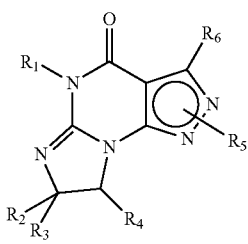

Formula Ia wherein
(i) $R_1$ is H or $C_{1-4}$ alkyl;
(ii) $R_4$ is H and $R_2$ and $R_3$ are, independently, H or $C_{1-4}$ alkyl, aryl, or arylalkyl;
(iii) $R_5$ is attached to one of the nitrogen atoms on the pyrazolo portion of formula Ia and is a substituted benzyl of formula B

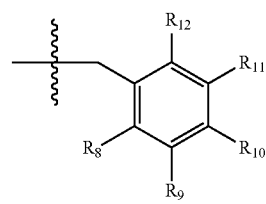

Formula B wherein $R_8$, $R_9$, $R_{11}$ and $R_{12}$ are independently H or halogen; and $R_{10}$ is halogen, alkyl, cycloalkyl, haloalkyl, aryl, heteroaryl, arylcarbonyl, or heteroarylcarbonyl, and
(iv) $R_6$ is H, alkyl, aryl, heteroaryl, arylalkyl, arylamino, heteroarylamino, N,N-dialkylamino, N,N-diarylamino, or N-aryl-N-(arylalkyl)amino;
wherein
aryl is optionally substituted with $C_{1-4}$alkyl, halogen, halo$C_{1-4}$alkyl, hydroxy, carboxy or an additional aryl or heteroaryl; and
heteroaryl is optionally substituted with $C_{1-4}$alkyl, halogen, halo$C_{1-4}$alkyl, hydroxy or carboxy;
in free, salt or physiological hydrolysable and acceptable ester prodrug form.

18. The method according to claim 17 wherein said compound is a compound

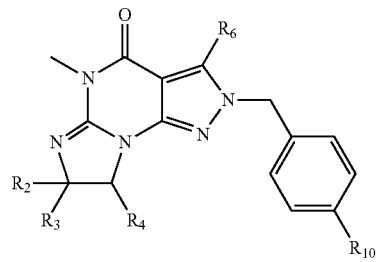

wherein
R$_2$ and R$_3$ are each methyl and R$_4$ is H; or R$_2$ and R$_4$ are H and R$_3$ is isopropyl;
R$_6$ is phenylamino;
R$_{10}$ is phenyl, pyridyl, or thiadiazolyl;
wherein:
phenyl is optionally substituted with C$_{1-4}$alkyl, halogen, haloC$_{1-4}$alkyl, hydroxy, carboxy or an additional aryl or heteroaryl; or
pyridyl and thiadiazolyl is optionally substituted with C$_{1-4}$alkyl, halogen, haloC$_{1-4}$alkyl, hydroxy or carboxy;
in free or salt form.

19. The method according to claim 13, selected from the following:
2-(Biphenyl-4-ylmethyl)-7,8-dihydro-5,7,7-trimethyl-[2H]-imidazo-[1,2-a]pyrazolo[4,3-e]pyrimidin-4(5H)-one;
3-Benzyl-2-(biphenyl-4-ylmethyl)-7,8-dihydro-5,7,7-trimethyl-[2H]-imidazo-[1,2-a]pyrazolo[4,3-e]pyrimidin-4(5H)-one;
1-(Biphenyl-4-ylmethyl)-7,8-dihydro-5,7,7-trimethyl-3-(phenylamino)-[1H]-imidazo-[1,2-a]pyrazolo[4,3-e]pyrimidin-4(5H)-one;
1-(4-(1,2,3-thiadiazol-4-yl)benzyl)-7,8-dihydro-5,7,7-trimethyl-3-(phenylamino)-[1H]-imidazo-[1,2-a]pyrazolo[4,3-e]pyrimidin-4(5H)-one;
1-(Biphenyl-4-ylmethyl)-3-((biphenyl-4-ylmethyl)(phenyl)amino)-7,8-dihydro-5,7,7-trimethyl-[1H]-imidazo-[1,2-a]pyrazolo[4,3-e]pyrimidin-4(5H)-one;
(R)-3-(Benzyl)-2-(biphenyl-4-ylmethyl)-7,8-dihydro-7-isopropyl-5-methyl-[2H]-imidazo-[1,2-a]pyrazolo[4,3-e]pyrimidin-4(5H)-one;
2-(Biphenyl-4-ylmethyl)-7,8,9-trihydro-5,8,8-trimethyl-3-(phenylamino)-[2H]-pyrimido-[1,2-a]pyrazolo[4,3-e]pyrimidin-4(5H)-one;
(7R)-2-(Biphenyl-4-ylmethyl)-7,8-dihydro-5,7-dimethyl-3-(phenylamino)-[2H]-imidazo-[1,2-a]pyrazolo[4,3-e]pyrimidin-4(5H)-one;
(8R)-2-(Biphenyl-4-ylmethyl)-7,8-dihydro-5,8-dimethyl-3-(phenylamino)-[2H]-imidazo-[1,2-a]pyrazolo[4,3-e]pyrimidin-4(5H)-one;
(7R)-2-(Biphenyl-4-ylmethyl)-7,8-dihydro-3-(phenylamino)-5-methyl-7-(1-methylethyl)-[2H]-imidazo-[1,2-a]pyrazolo[4,3-e]pyrimidin-4(5H)-one;
in free or salt form, or in pure enantiomeric form.

\* \* \* \* \*